US 8,353,961 B2

(12) United States Patent
McClintock et al.

(10) Patent No.: US 8,353,961 B2
(45) Date of Patent: Jan. 15, 2013

(54) EXPANDABLE VERTEBRAL DEVICE WITH CAM LOCK

(75) Inventors: Larry McClintock, Gore, VA (US); Kevin R. Strauss, Columbia, MD (US); Atiq Durrani, Cincinnati, OH (US)

(73) Assignee: K2M, Inc., Leesburg, VA (US)

( * ) Notice: Subject to any disclaimer, the term of this patent is extended or adjusted under 35 U.S.C. 154(b) by 520 days.

(21) Appl. No.: 12/366,805

(22) Filed: Feb. 6, 2009

(65) Prior Publication Data

US 2009/0204215 A1    Aug. 13, 2009

Related U.S. Application Data

(60) Provisional application No. 61/063,895, filed on Feb. 7, 2008, provisional application No. 61/086,953, filed on Aug. 7, 2008.

(51) Int. Cl.
*A61F 2/44* (2006.01)

(52) U.S. Cl. ................................... 623/17.15

(58) Field of Classification Search ..... 623/17.11–17.16
See application file for complete search history.

(56) References Cited

U.S. PATENT DOCUMENTS

| | | | | |
|---|---|---|---|---|
| 5,458,641 | A * | 10/1995 | Ramirez Jimenez | 623/17.11 |
| 5,901,798 | A * | 5/1999 | Herrera et al. | 175/325.3 |
| 6,176,881 | B1 * | 1/2001 | Schar et al. | 623/17.11 |
| 6,193,755 | B1 * | 2/2001 | Metz-Stavenhagen et al. | 623/17.11 |
| 6,200,348 | B1 * | 3/2001 | Biedermann et al. | 623/17.11 |
| 6,440,170 | B1 * | 8/2002 | Jackson | 623/17.16 |
| 6,866,682 | B1 * | 3/2005 | An et al. | 623/17.15 |
| 7,531,002 | B2 * | 5/2009 | Sutton et al. | 623/17.15 |
| 7,691,147 | B2 * | 4/2010 | Gutlin et al. | 623/17.15 |
| 2003/0181980 | A1 | 9/2003 | Berry et al. | |
| 2005/0085910 | A1 * | 4/2005 | Sweeney | 623/17.11 |
| 2005/0273173 | A1 * | 12/2005 | Gordon et al. | 623/17.16 |
| 2006/0100710 | A1 * | 5/2006 | Gutlin et al. | 623/17.15 |
| 2006/0149385 | A1 * | 7/2006 | McKay | 623/17.15 |
| 2006/0200244 | A1 * | 9/2006 | Assaker | 623/17.15 |
| 2007/0100340 | A1 * | 5/2007 | Lange et al. | 606/61 |
| 2007/0162126 | A1 * | 7/2007 | Karahalios et al. | 623/17.11 |

(Continued)

FOREIGN PATENT DOCUMENTS

DE        19804765 A1    8/1999

(Continued)

OTHER PUBLICATIONS

European Search Report dated May 28, 2009 from corresponding EP Appln. No. EP09152270.6 filed Feb. 6, 2009.

*Primary Examiner* — Alvin Stewart
*Assistant Examiner* — Jacqueline Johanas
(74) *Attorney, Agent, or Firm* — Carter, DeLuca, Farrell & Schmidt LLP

(57) ABSTRACT

An expandable cage supports adjacent vertebra in spine surgery. The expandable cage includes a first supporting member configured to engage tissue and a second supporting member operatively associated with the first supporting member. The first and second supporting members are movable relative to each other. The expandable cage further includes a cam lock mechanism configured to maintain the first and second supporting members in a fixed relative position. In another embodiment, the expandable cage includes a ring plate lock mechanism in lieu of the cam lock mechanism. The ring plate lock mechanism is adapted to maintain the first and second supporting members in a fixed relative position.

16 Claims, 22 Drawing Sheets

U.S. PATENT DOCUMENTS

| | | | |
|---|---|---|---|
| 2007/0191954 A1* | 8/2007 | Hansell et al. | 623/17.15 |
| 2008/0009946 A1 | 1/2008 | Douget et al. | |
| 2008/0114467 A1* | 5/2008 | Capote et al. | 623/23.47 |
| 2008/0125864 A1* | 5/2008 | de Villiers et al. | 623/17.15 |
| 2008/0167720 A1* | 7/2008 | Melkent | 623/17.16 |
| 2008/0288071 A1* | 11/2008 | Biyani et al. | 623/17.11 |

FOREIGN PATENT DOCUMENTS

| | | |
|---|---|---|
| FR | 2902315 A | 12/2007 |
| WO | WO 98/46173 A | 10/1998 |
| WO | WO 2008/005627 A2 | 1/2008 |
| WO | WO 2009/023016 A | 2/2009 |

* cited by examiner

EXPANDABLE VERTEBRAL DEVICE WITH CAM LOCK

CROSS-REFERENCE TO RELATED APPLICATIONS

The present application claims priority and the benefit of U.S. Provisional Patent Application No. 61/063,895, filed on Feb. 7, 2008, and U.S. Provisional Patent Application No. 61/086,953, filed on Aug. 7, 2008, each of which is incorporated herein by reference in its entirety.

BACKGROUND

1. Technical Field

The present disclosure relates to apparatus and methods for treating spinal conditions and, more particularly, for supporting adjacent vertebrae.

2. Background of Related Art

The human spine includes thirty-three vertebrae. The vertebrae interlock with one another to form a spinal column. Each vertebra has a cylindrical bony body (vertebral body), two pedicles extending from the vertebral body, a lamina extending from the pedicles, two wing-like projections extending from the pedicles, a spinous process extending from the lamina, a pars interarticularis, two superior facets extending from the pedicles, and two inferior facets extending from the lamina. The vertebrae are separated and cushioned by thin pads of tough, resilient fiber known as intervertebral discs. Intervertebral discs provide flexibility to the spine and act as shock absorbers during activity. A small opening (foramen) located between each vertebra allows passage of nerves. When the vertebrae are properly aligned, the nerves pass through without a problem. However, when the vertebrae are misaligned or a constriction is formed in the spinal canal, the nerves get compressed and may cause back pain, leg pain, or other neurological disorders.

Disorders of the spine that may cause misalignment of the vertebrae or constriction of the spinal canal include spinal injuries, infections, tumor formation, herniation of the intervertebral discs (i.e., slippage or protrusion), arthritic disorders, and scoliosis. In these pathologic circumstances, surgery may be tried to either decompress the neural elements and/or fuse adjacent vertebral segments. Decompression may involve laminectomy, discectomy, or corpectomy. Laminectomy involves the removal of part of the lamina, i.e., the bony roof of the spinal canal. Discectomy involves removal of the intervertebral discs. Corpectomy involves removal of the vertebral body as well as the adjacent intervertebral discs.

A number of spinal surgical devices may be used to promote bony fusion after decompressing the spinal nerves. For instance, surgeons often replace the diseased vertebral tissue with one or more spinal cages and bone support matrix. Spinal cages support adjacent vertebral segments, while furthering spinal fusion of the adjacent vertebral bodies. Scientists and clinicians have developed a number of devices and methods for decompressing spinal nerves. Improvements to these methods and devices are nevertheless still possible.

SUMMARY

The present disclosure relates to an expandable cage for supporting adjacent vertebra. The expandable cage includes a first supporting member configured to engage tissue and a second supporting member operatively associated with the first support member. The first and second supporting members are movable relative to each other. The expandable cage further includes a cam lock mechanism configured to maintain the first and second supporting members in a fixed relative position.

The present disclosure further relates to an apparatus for spinal surgery. This apparatus includes a first supporting member configured to engage tissue and a second supporting member operatively associated with the first supporting member. The first and second supporting members are adapted to move relative to each other. The apparatus further includes a ring plate lock mechanism configured to maintain the first and second supporting members in a fixed relative position.

The present disclosure also relates to an apparatus for spinal surgery including a first member configured to engage tissue, a second member configured to engage tissue, a telescoping support member operatively associated with the first and second members, such that the first and second members are movable relative to each other; and a lock mechanism associated with the telescoping support member and configured to maintain the first and second members in a fixed relative position.

DETAILED DESCRIPTION OF THE EMBODIMENTS

Figure 1:
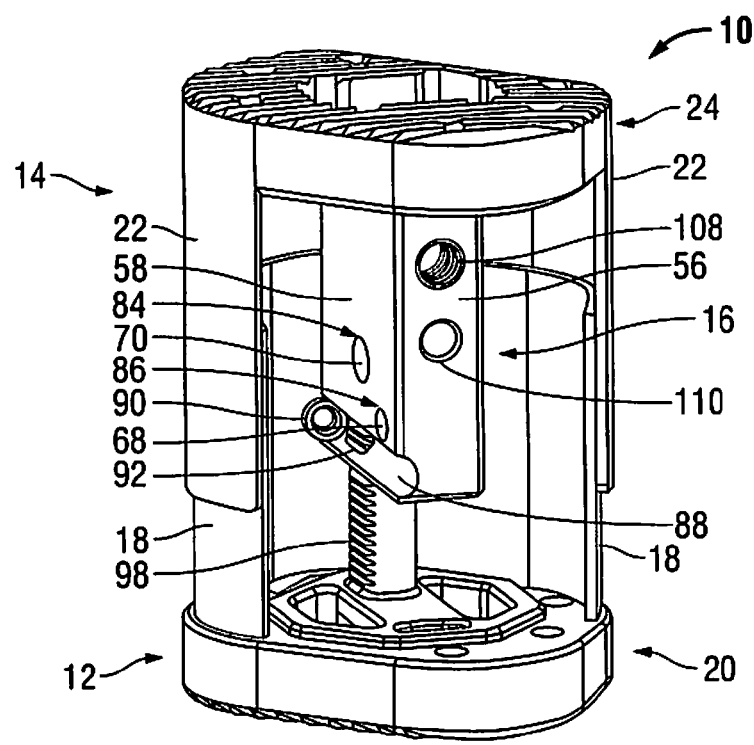
FIG. 1 is a perspective view of an expandable cage according to an embodiment of the present disclosure.

Embodiments of the presently disclosed devices and methods will now be described in detail with reference to the drawings, wherein like reference numerals identify similar or identical elements. In the drawings and in the description that follows, the term "proximal" will refer to the end of an expandable cage or tool that is closest to the operator, while the term "distal" will refer to the end of the expandable cage or tool that is farthest from the operator. In addition, the term "cephalad" is used in this application to indicate a direction toward a patient's head, whereas the term "caudad" indicates a direction toward the patient's feet. Further still, for the purposes of this application, the term "medial" indicates a direction toward the middle of the body of the patient, whilst the term "lateral" indicates a direction toward a side of the body of the patient (i.e., away from the middle of the body of the patient). The term "posterior" indicates a direction toward the patient's back, and the term "anterior" indicates a direction toward the patient's front. As used herein, a "bone support matrix" is a material that facilitates new bone growth between the opposing vertebral bodies. Suitable bone support matrices can be resorbable or nonresorbable and osteoconductive or osteoinductive. Examples of suitable bone support matrices include synthetic materials, bone morphogenic proteins (BMPs), and heterologous, homologous, or autologous bone and derivatives thereof. The bone support matrix may be radiolucent on x-rays.

With reference to FIGS. 1-4, an expandable cage 10, which may be made (wholly or partially) of metal, polyetheretherketone (PEEK) or any other suitable material, generally includes first and second supporting members 12, 14 and a connecting member 16. First and second supporting members 12, 14 are slidably coupled to each other, and connecting member 16 maintains a predetermined spacing between first and second supporting members 12, 14. First supporting member 12 contains a first wall 18 partially surrounding connecting member 16 and an oblong-shaped first supporting end or plate 20 configured to engage vertebral tissue or any other kind of tissue. Second support member 14 features a second wall 22 partially surrounding connecting member 16 and an oblong-shaped second supporting end or plate 24 adapted to engage vertebral tissue or any other kind of tissue. Second wall 22 slidably receives first wall 18 therein. As a consequence, first and second supporting members 12, 14 are capable of sliding or moving with respect to each other. In operation, first and second supporting members 12, 14 can move between a collapsed position (see FIG. 10) and an expanded position (see FIG. 1) to engage vertebral tissue. It is envisioned that expandable cage 10 may be made of metal. Some portions of expandable cage, however, may be made of non-metallic materials such as PEEK. In one embodiment, the entire expandable cage 10 is made of metal, except for first and second supporting plates 20, 24, which are made of PEEK.

First and second supporting plates 20, 24 directly engage vertebral tissue when expandable cage 10 is implanted between adjacent vertebrae during a spinal surgical procedure. First supporting plate 20 includes a first engagement surface 26 adapted to engage tissue, a first coupling surface 28 for securing first supporting plate 20 to connecting member 16, and an opening 116 for allowing passage of bone support matrix therethrough. (See FIGS. 9 and 16). First engagement surface 26 defines an oblique angle relative to coupling surface 28 and has a plurality of teeth 30 protruding therefrom. Teeth 30 are arranged in longitudinal rows extending the width of first engagement surface 26. Each tooth 30 defines an oblique angle in relation to first engagement surface 26. During spinal surgery, teeth 30 frictionally engage vertebral tissue to secure first support plate 20 to a vertebra.

Second supporting plate 24 engages another vertebra during use and includes a second engagement surface 32 configured for engaging tissue, a second coupling surface 34 for securing second support plate 24 to connecting member 16, and an opening 118 for allowing passage of bone support matrix therethrough. Second engagement surface 32 defines an oblique angle relative to second coupling surface 34 and has a plurality of teeth 35 protruding therefrom. Teeth 35 are arranged in longitudinal rows spanning the width of second engagement surface 32. Each tooth 35 defines an oblique angle with respect to second engagement surface 32. In operation, teeth 35 frictionally engage vertebral tissue to secure second support plate 24 to a vertebra. The user might need to move first and second support members 12, 14 relative to each other to contact the adjacent vertebrae with teeth 30, 35 of first and second support plates 20, 24.

Figure 8:
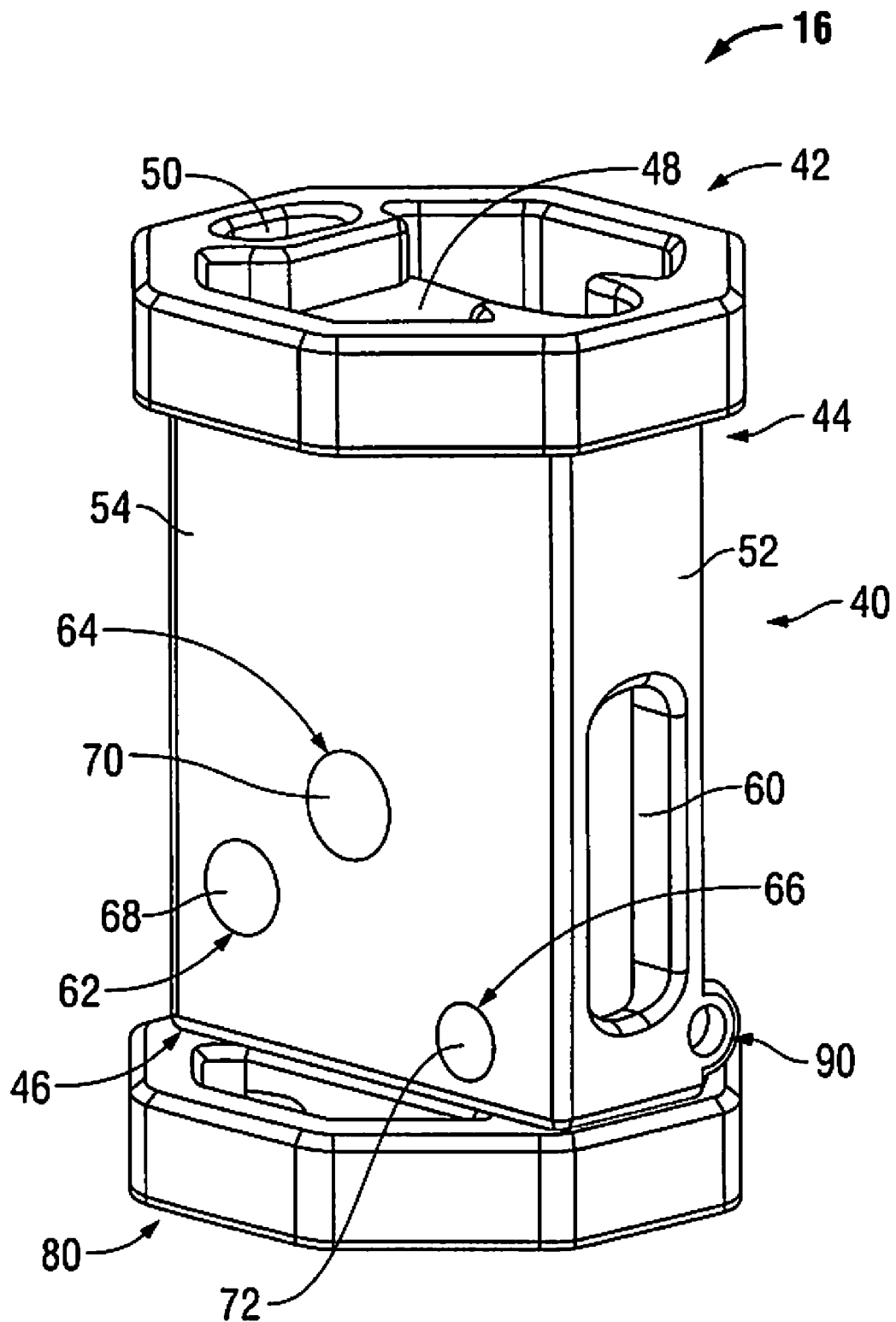
FIG. 8 is a perspective view of the completely assembled connecting member of FIG. 7.

With reference to FIGS. 5-8, connecting member 16 features first and second movable structures 36, 38 adapted to slide relative to each other. In general, first movable structure 36 includes an elongate body 40 having first and second ends 44, 46 and a first octagonal panel 42. First octagonal panel 42, which is attached to the first end 44 of elongate body 40, contains an opening 48 for allowing passage of bone support matrix therethrough and an opening 50 for receiving and securing another portion of second support plate 24 (See FIG. 18). As shown in FIG. 8, opening 50 has an elliptical cross-section.

Figure 5:
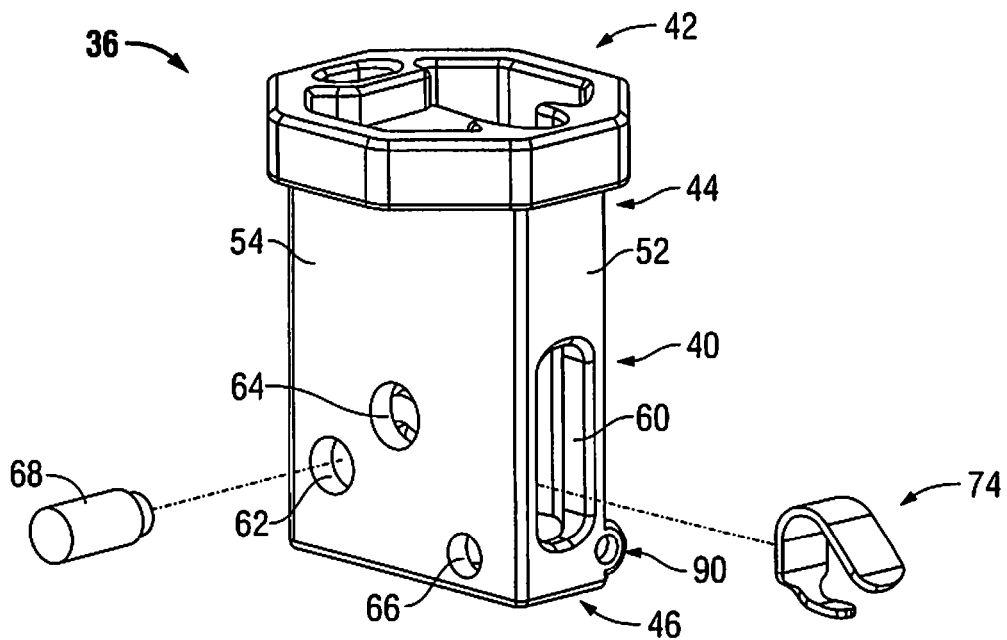
FIG. 5 is a perspective exploded view of a portion of a connecting member with a biasing member and pin for coupling the biasing member to the connecting member.
Figure 6:
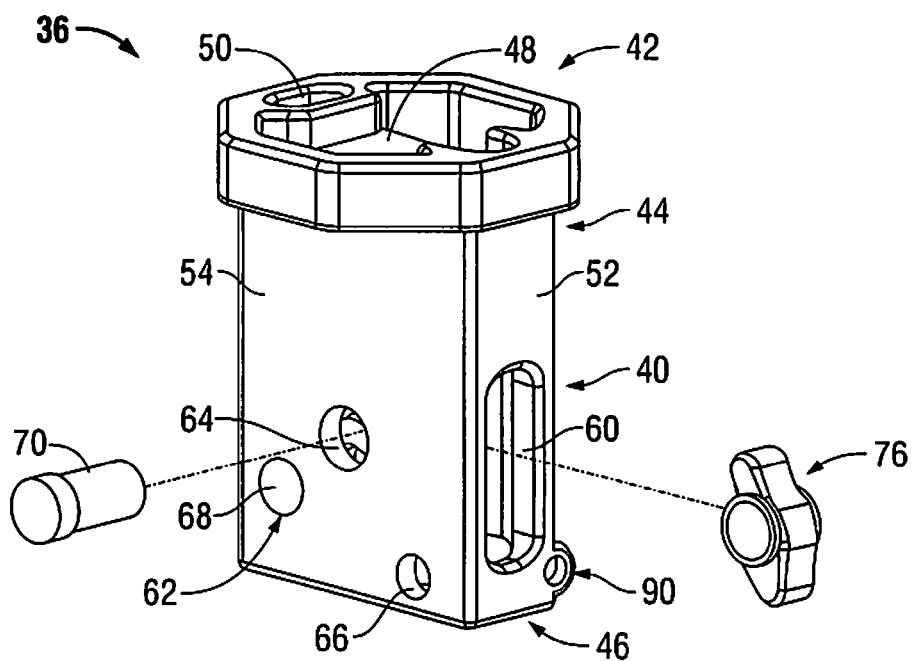
FIG. 6 is a perspective exploded view of a portion of the connecting member of FIG. 5 with a camming member and a pin for coupling the camming member to the connecting member.
Figure 7:
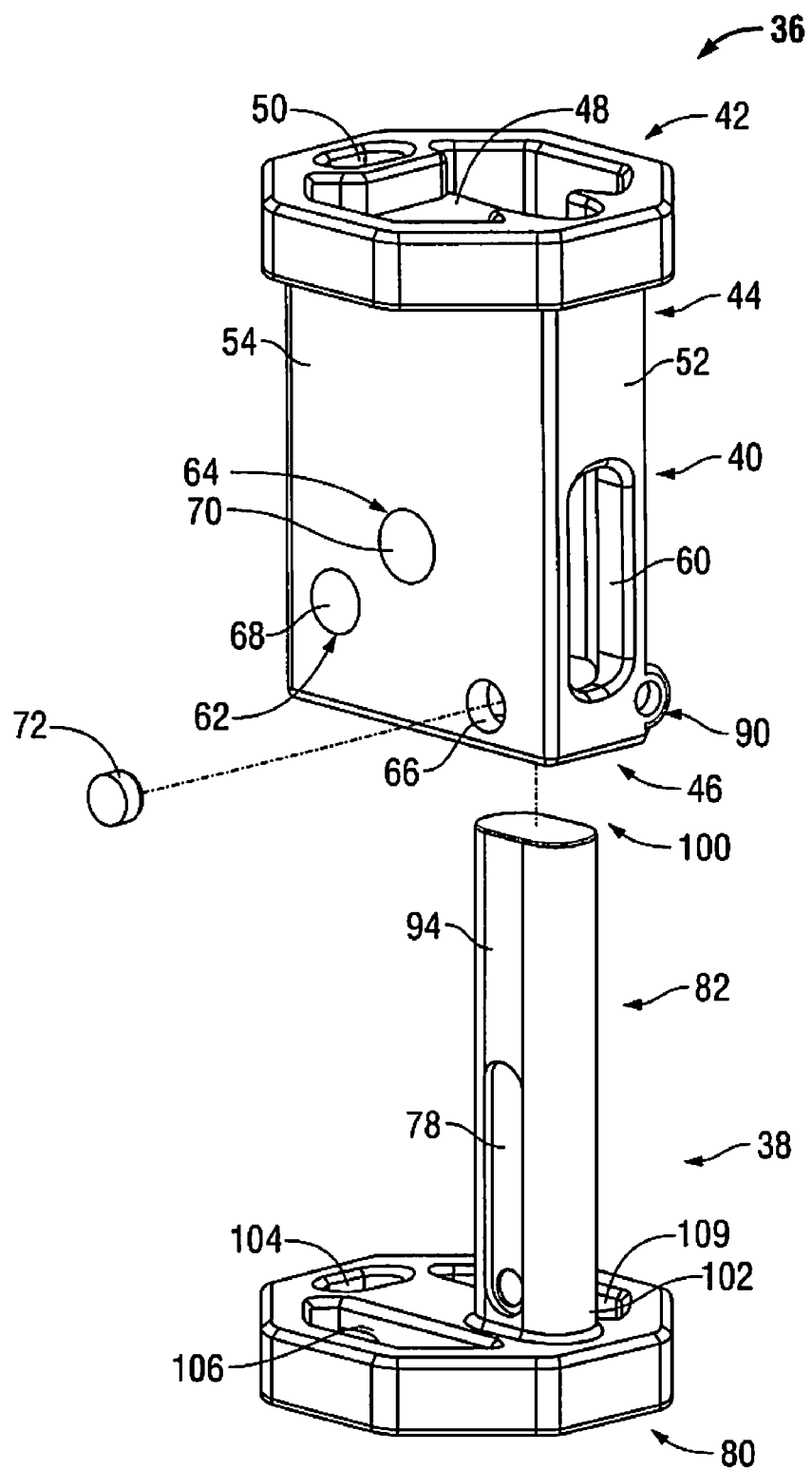
FIG. 7 is a perspective exploded view of a connecting member of the expandable cage of FIG. 1, showing a panel and a pin for slidably connecting the panel to the connecting member.

Elongate body 40 has a rectangular configuration. It is contemplated that elongate body 40 may have other configurations including circular, oval, or another geometric shape. First, second, third, and fourth walls 52, 54, 56, 58 partially form elongate body 40. (See FIGS. 1 and 8). First and third walls 52, 56 are substantially parallel to each other. Similarly, second and fourth 54, 58 are substantially parallel to each other. Thus, first and third walls 52, 56 are substantially perpendicular to second and fourth walls 54, 58. First wall 52 defines an elongate opening 60 for facilitating assembly of connecting member 16 and a ring 90 disposed on second end 46 of elongate body 40. Ring 90 inhibits elongate pinion 234 (see FIG. 14) from moving distally beyond the boundaries of elongate body 40. Ring 90 further provides support for instrument 200 (FIG. 14) such that the instrument 200 does not disengage during use. In particular, a manufacturer may insert a biasing member 74 and a camming member 76 into elongate body 40 through opening 60, as illustrated in FIGS. 5 and 6. Second wall 54 includes first hole 62 dimensioned for receiving holding pin 68, a second hole 64 dimensioned for receiving pivot pin 70, and a third hole 66 dimensioned for receiving sliding pin 72.

As seen in FIGS. 15-18, holding pin 68 retains biasing member 74 within a cavity 112 (FIG. 18) of elongate body 40. Biasing member 74 may be a spring or any other suitable device or apparatus. Pivot pin 70 pivotally connects camming member 76 to elongate body 40. Camming member 76, which is located inside elongate body 40, pivots about pivot pin 70 upon actuation of a tool 200, as discussed in detail below. Sliding pin 72 is configured to slide along a slot 78 formed on a portion of second movable structure 38.

Referring again to FIGS. 1 and 5-8, third wall 56 includes a threaded hole 108 adapted for receiving a threaded portion of tool 200 and an opening 110 extending into a cavity 112 disposed within elongate body 40. (See FIG. 18). Holding pin 68, biasing member 74, pivot pin 70, and camming member 76 are all at least partially positioned inside cavity 112 of elongate body 40 and together form a cam lock mechanism 128 configured to maintain the first and second movable structures 36, 38 in a fixed relative position. Fourth wall 58 of elongate body 40 includes a fourth hole 84 for receiving pivot pin 70 and a fifth hole 86 for receiving holding pin 68. In addition, fourth wall 58 has an arc-shaped recess 88 extending therealong. Arc-shaped recess 88, which is disposed on second end 46 of elongate body 40, is substantially aligned with ring 90. Furthermore, arc-shaped recess 88 has an opening 92 uncovering a portion of second movable structure 38.

Figure 2:
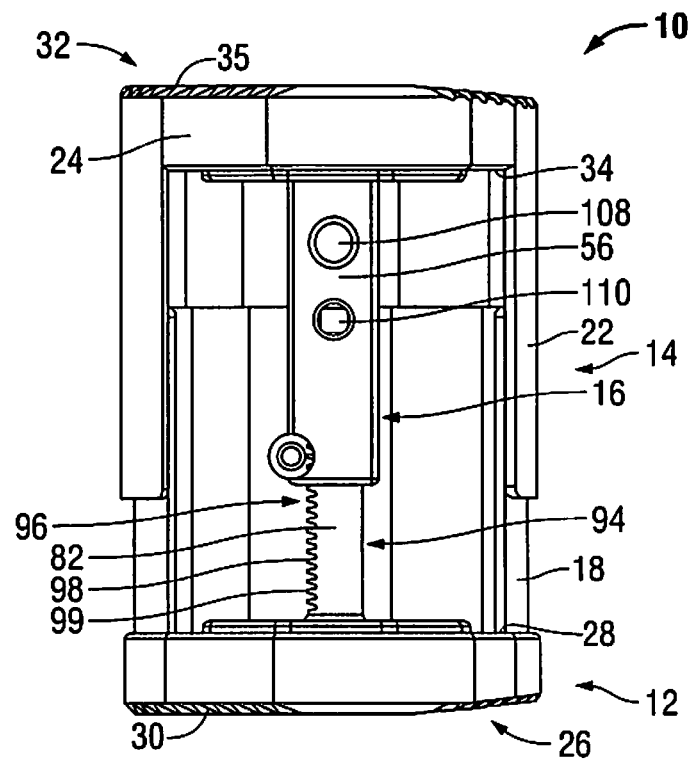
FIG. 2 is a front view of the expandable cage of FIG. 1.
Figure 3:
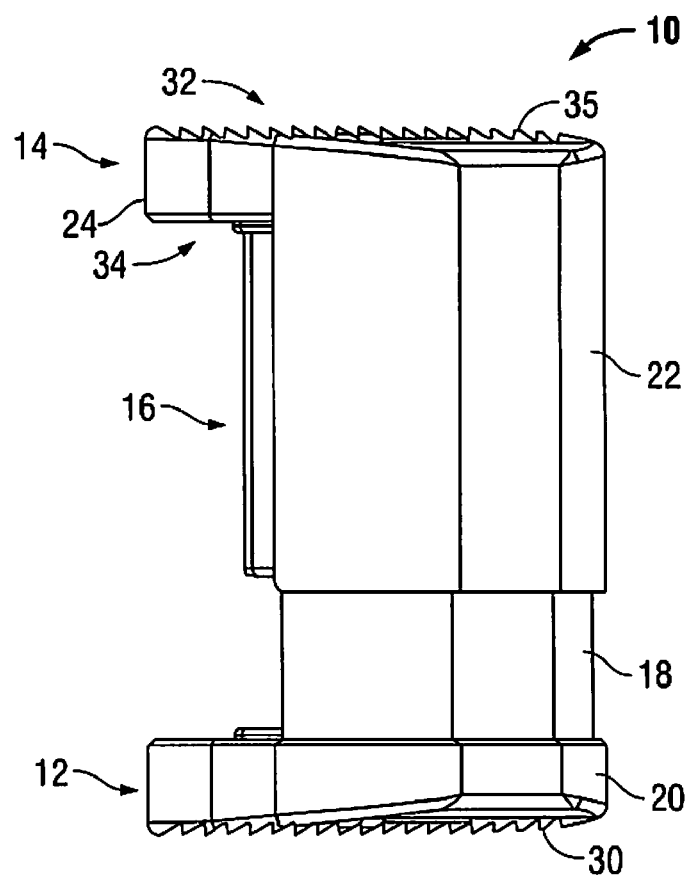
FIG. 3 is a side view of the expandable cage of FIG. 1.
Figure 4:
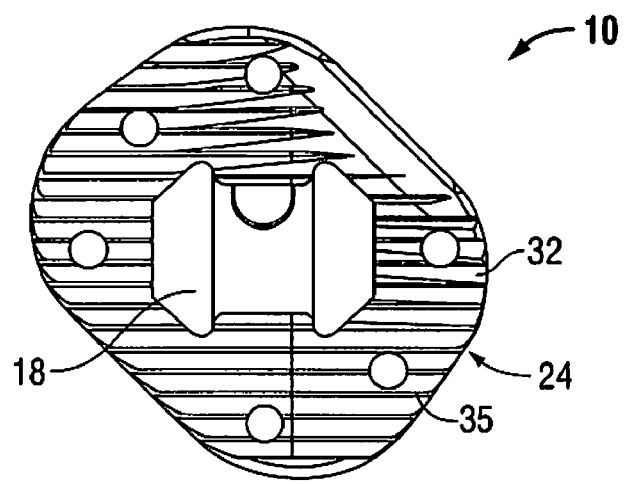
FIG. 4 is a top view of the expandable cage of FIG. 1.

Second movable structure 38 includes a second octagonal panel 80 and a column 82 having an elliptical profile. Second octagonal panel 80 includes an opening 104 for receiving and securing a portion of first support plate 20 and a pair of openings 106, 109 for allowing passage of bone support matrix. Column 82 has opposite lateral sides 94, 96, as seen in FIG. 2, a first free end 100, and a second end 102 attached to second octagonal panel 80. Slot 78 is formed in lateral side 94, while a rack 98 with teeth 99 (FIG. 2) is disposed along lateral side 96. Column 82 is configured to be slidably received within a longitudinal opening 114 of elongate body 40 (See FIG. 18). Longitudinal opening 114 extends between first and second ends 44, 46 of elongate body 40 and allows first and second movable structures 36, 38 to move relative to each other. Hence, the structural relationship of first and second movable structures 36, 38 permits connecting member 16 to slidably support first support member 12 and second supporting member 14.

To assemble connecting member 16, biasing member 74 is inserted into cavity 112 (see FIG. 18) through opening 60 and then holding pin 68 is inserted through first hole 62 to secure biasing member 74 to elongate body 40. (See FIG. 5). Subsequently, camming member 76 is positioned in cavity 112 through opening 60 and pivot pin 70 is introduced through second hole 64 to pivotally hold camming member 76. (See FIG. 6). Next, column 82 is positioned within longitudinal opening 114 (See FIG. 18) to slidably connect first movable structure 36 to second movable structure 38. (See FIG. 7).

Figure 9:
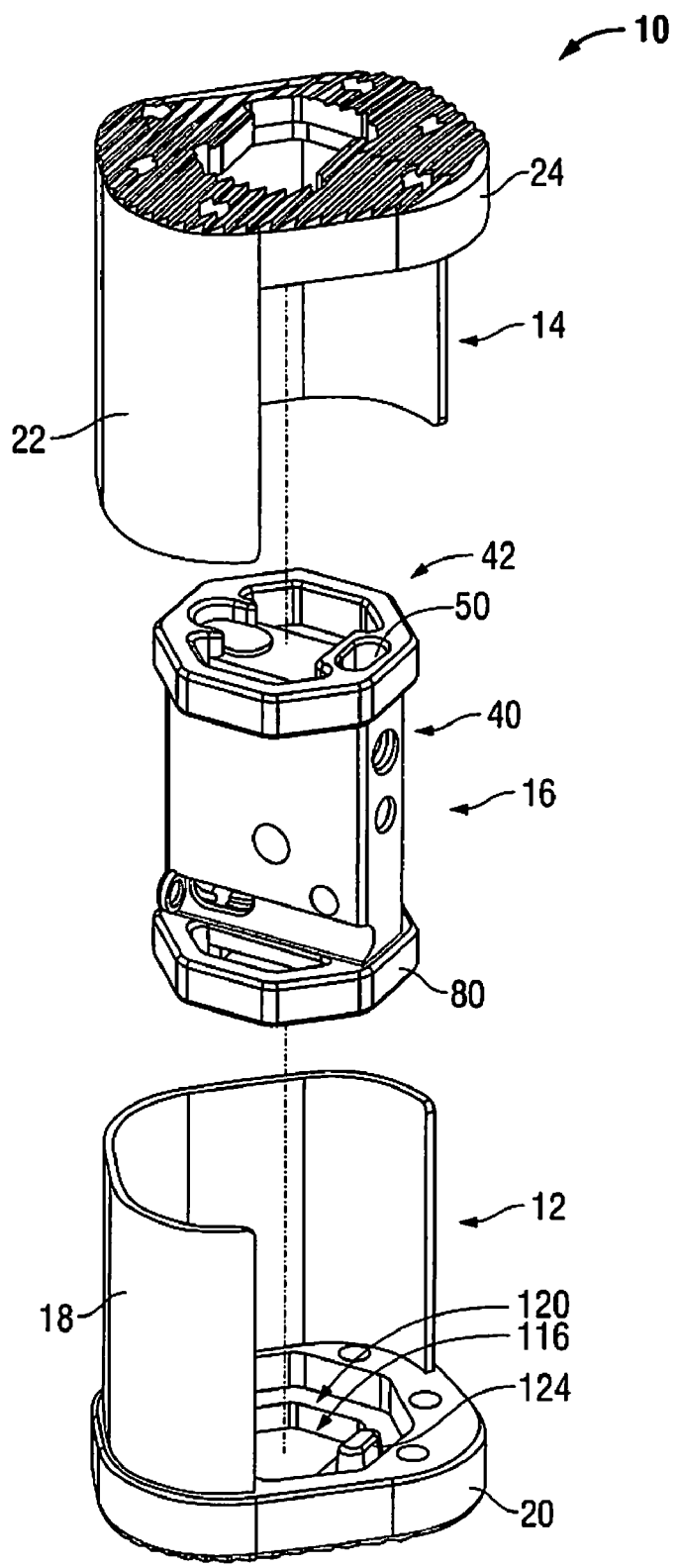
FIG. 9 is a perspective exploded view of the expandable cage of FIG. 1.
Figure 10:
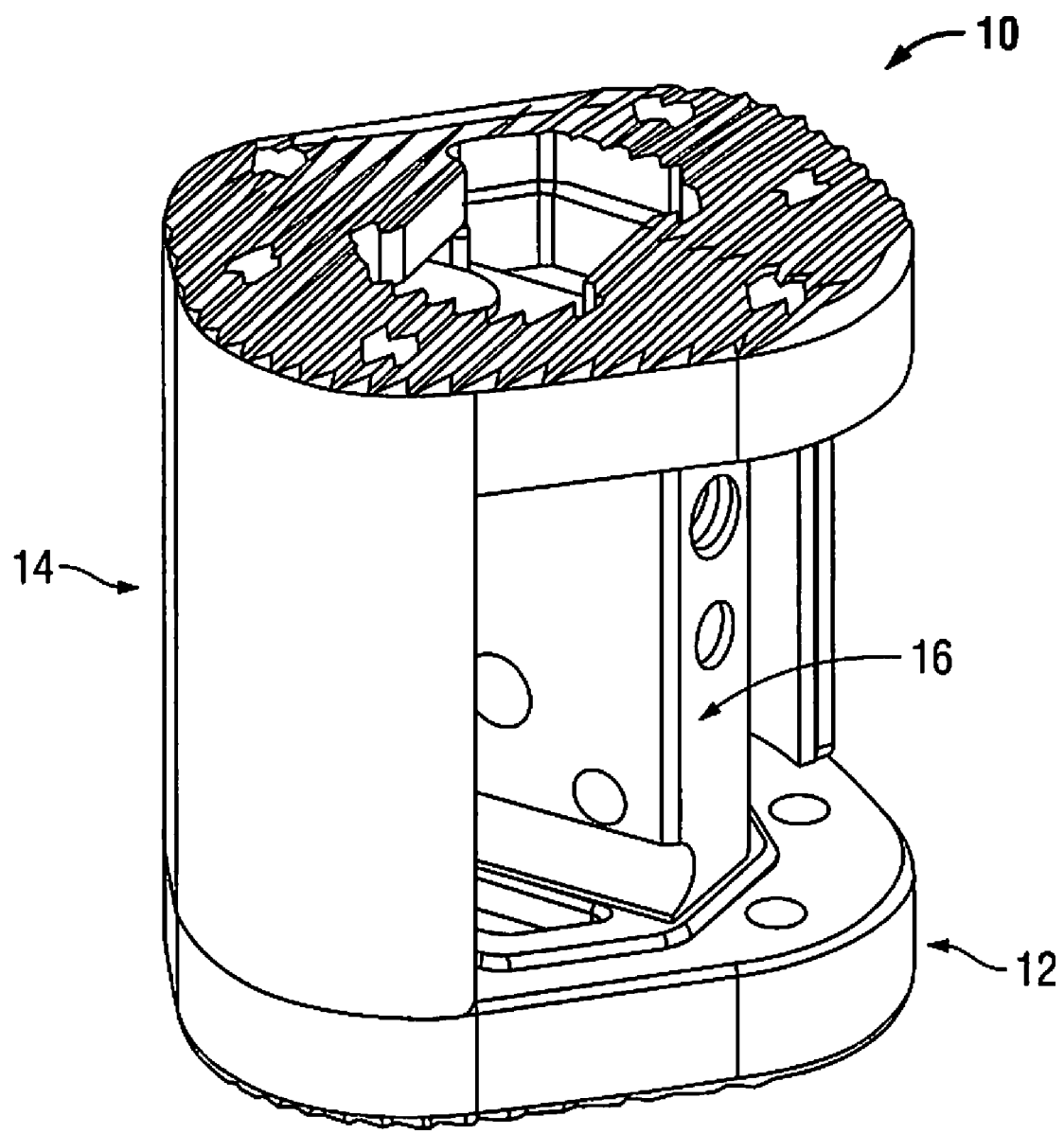
FIG. 10 is a perspective view of the expandable cage of FIG. 1 in a collapsed position.
Figure 16:
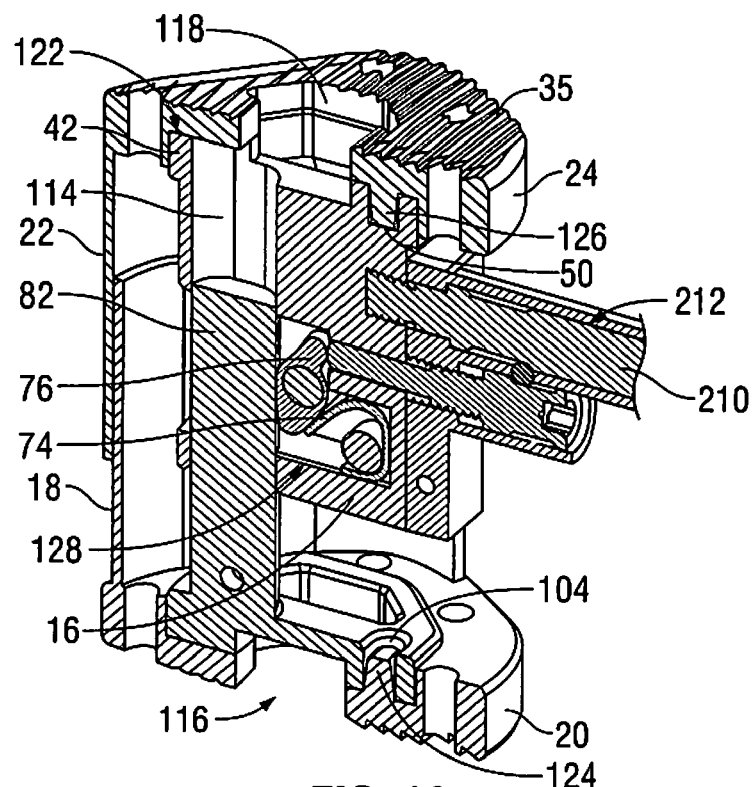
FIG. 16 is a perspective cross-sectional view of a portion of the tool of FIG. 11 attached to the expandable cage of FIG. 1, showing a cam lock mechanism in the locked position.
Figure 17:
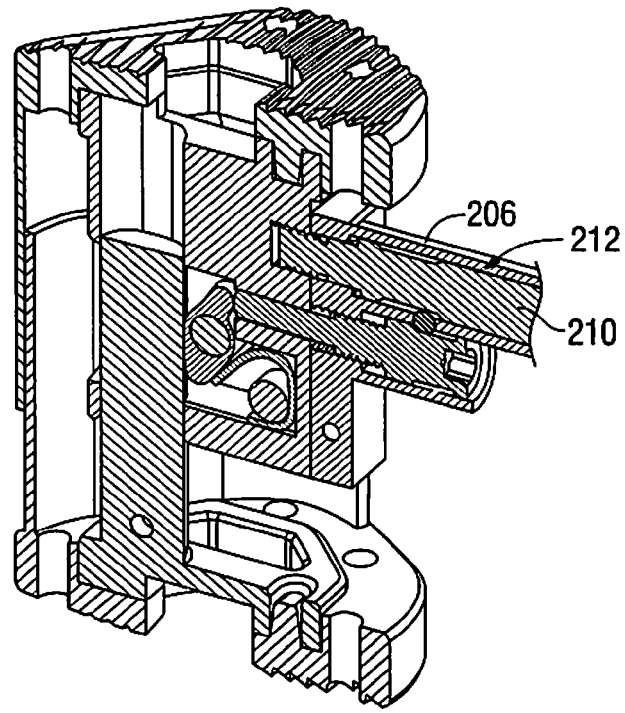
FIG. 17 is a perspective cross-sectional view of the tool of FIG. 11 attached to the expandable cage of FIG. 1, showing the cam lock mechanism in the locked position after re-adjusting the expandable cage.

With reference to FIGS. 9, 10, and 16, connecting member 16 can be operatively connected to first and second supporting members 12, 14 after it has been assembled as described above. First and second support plates 20, 24 of first and second supporting members 12, 14 have recesses 120, 122 disposed around an inner surface thereof for aiding in the assembly of expandable cage 10 (See also FIG. 16). Recess 122, which surrounds opening 118, is configured to securely receive first octagonal panel 42, as seen in FIG. 16. The shape of recess 122 is substantially similar to the shape of first octagonal panel 42. Recess 120, which encircles opening 116, is adapted to securely receive second octagonal panel 80. The shape of recess 120 mirrors the shape of second octagonal panel 80.

Recesses 120, 122 cooperate with first and second octagonal panels 42, 80 of connecting member 16 to align first and second supporting members 12, 14 with connecting member 16 in one particular orientation. When first and second supporting members 12, 14 are aligned with connecting member 16, expandable cage 10 can be properly assembled. As appreciated from FIG. 9, expandable cage 10 can only be correctly assembled in one orientation.

First support plate 20 further includes protrusion 124 extending from recess 120. Protrusion 124 is adapted to be received within opening 104 of second octagonal panel 80. (See FIG. 16). Second support plate 24 also includes a protrusion 126 extending from recess 122. Protrusion 126 is adapted to be received within opening 50 of first octagonal panel 42. During the assembly of expandable cage 10, protrusions 124, 126 help maintain connecting member 16 coupled to the first and second supporting members 12, 14.

Connecting member 16 is attached to first and second supporting members 12, 14 by first placing second octagonal panel 80 within recess 120 such that protrusion 124 passes through opening 104. Similarly, second supporting member 14 is placed over connecting member 16 by sliding second wall 22 along an outer surface of first wall 18 of first supporting member 12. As second support member 14 is positioned over connecting member 16, first octagonal panel 42 of connecting member 16 enters into recess 122 of second support member 14 and protrusion 126 passes through opening 50. After the assembly has been completed, second wall 22 of first supporting member 12 rests on an edge of second supporting plate 20 when expandable cage 10 is in the collapsed position, as illustrated in FIG. 10. Alternatively, wall 22 may be spaced apart from plate 20 defining a gap therebetween. A user can expand expandable cage 10 with the aid of tool 200 or any other suitable device or instrument (See FIG. 13).

Figure 11:
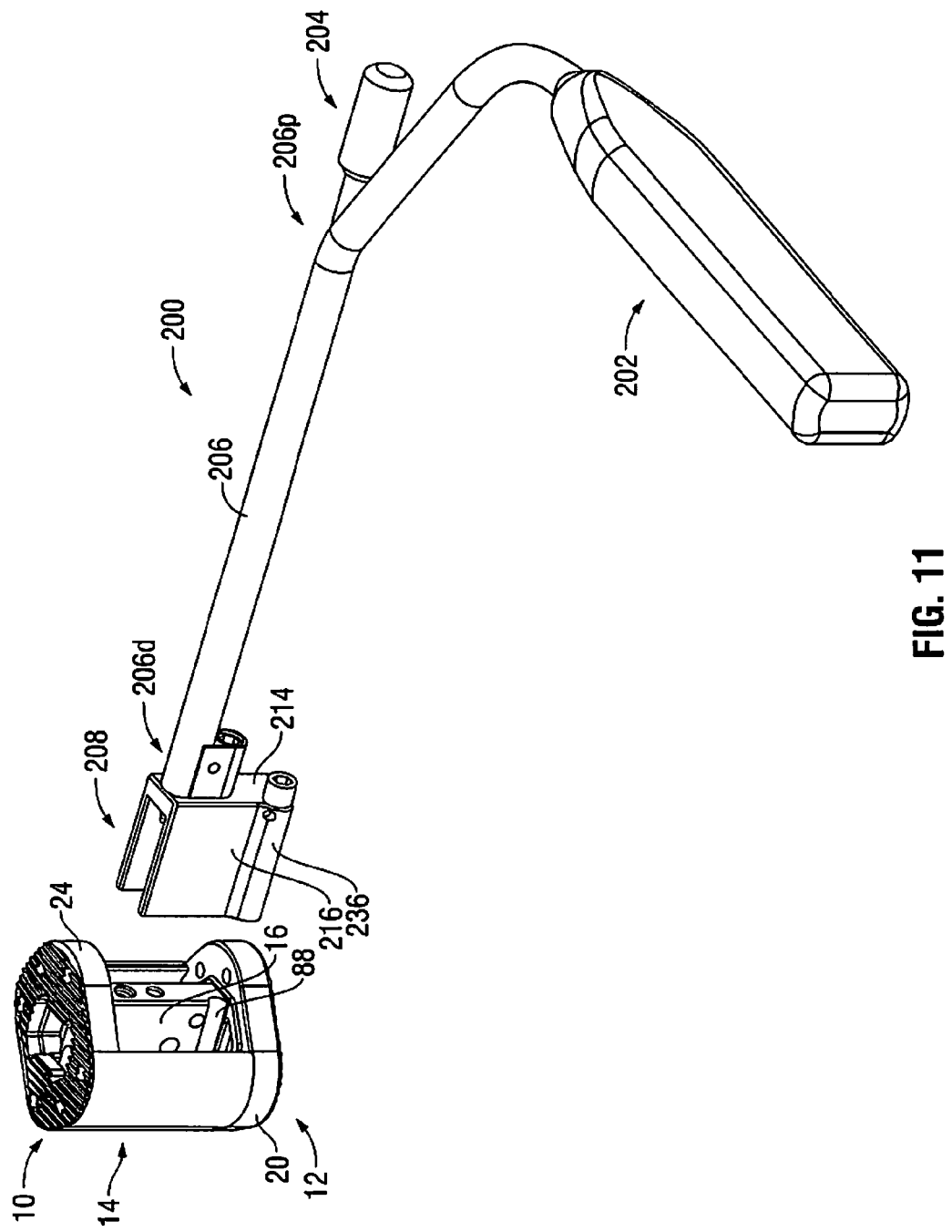
FIG. 11 is a perspective view of the expandable cage of FIG. 1 and a tool for inserting and expanding the expandable cage.
Figure 12:
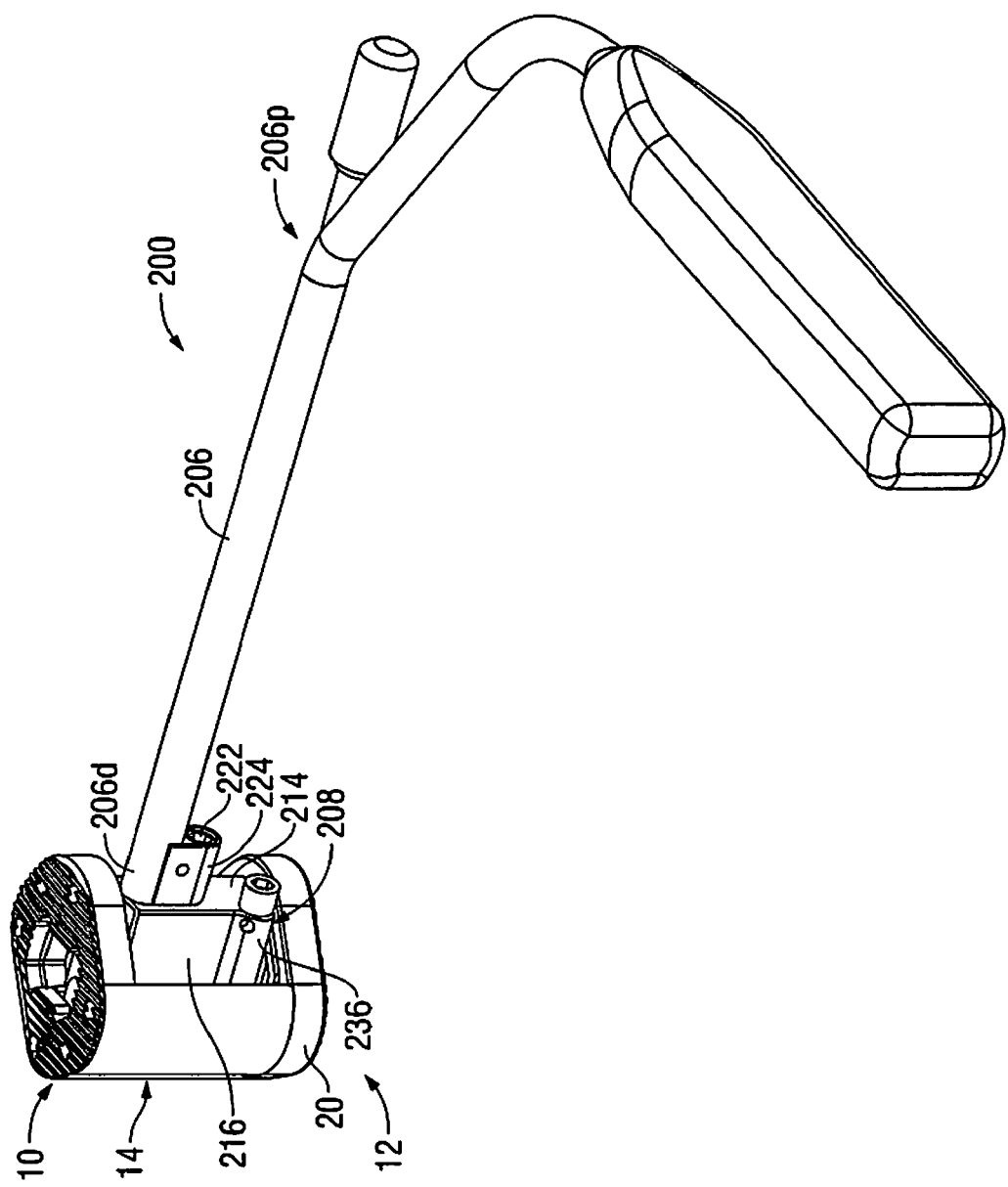
FIG. 12 is a perspective view of the tool of FIG. 11 attached to the expandable cage of FIG. 1.

With reference to FIGS. 11 and 12, a tool 200 designed for inserting and expanding expandable cage 10 includes first and second handles 202, 204, a holding portion 208, and an elongate body 206 interconnecting holding portion 208 with first and second handles 202, 204. Elongate body 206 has proximal and distal ends 206p, 206d. First and second handles 202, 204 are attached to the proximal end 206p of elongate body 206. Particularly, first handle 202 extends transversely from elongate body 206. Although second handle 204 also extends from elongate body 206, second handle 204 is substantially parallel to elongate body 206. In addition, first handle 202 is fixedly coupled to elongate body 206, while second handle 204 is rotatably connected to elongate body 206. Second handle 204 is operatively connected to a rod 210 positioned inside elongate body 206. (See FIG. 15). Elongate body 206 defines a bore 212 extending therethrough. Bore 212 of elongate body 206 is adapted to slidably receive rod 210. Rod 210 includes a distal portion 210d having a threaded section 210t (See FIG. 18).

Holding portion 208 is fixed to proximal end 206d of elongate body 206 and is adapted to hold connecting member 16, as seen in FIG. 12. In general, holding portion 208 includes a proximal wall 214 and a pair of arms 216 extending distally from proximal wall 214. Arms 216 define a space therebetween dimensioned to receive elongate body 40 of connecting member 16.

Figure 18:
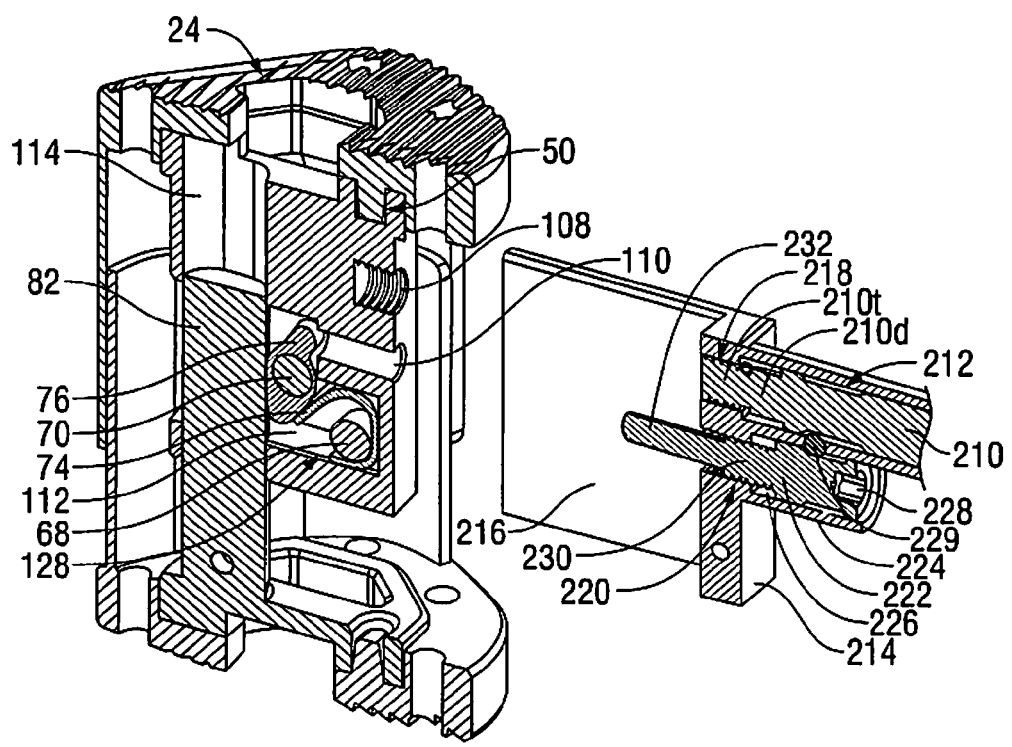
FIG. 18 is a perspective cross-sectional view of the tool of FIG. 11 detached from the expandable cage of FIG. 1, showing the cam lock mechanism in a locked position.
Figure 19:
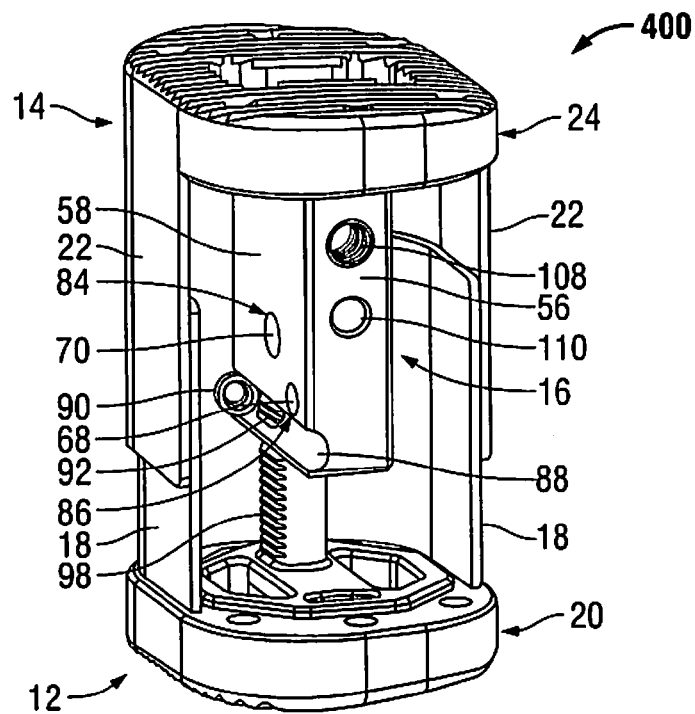
FIG. 19 is a perspective view of an expandable cage according to another embodiment of the present disclosure.
Figure 20:
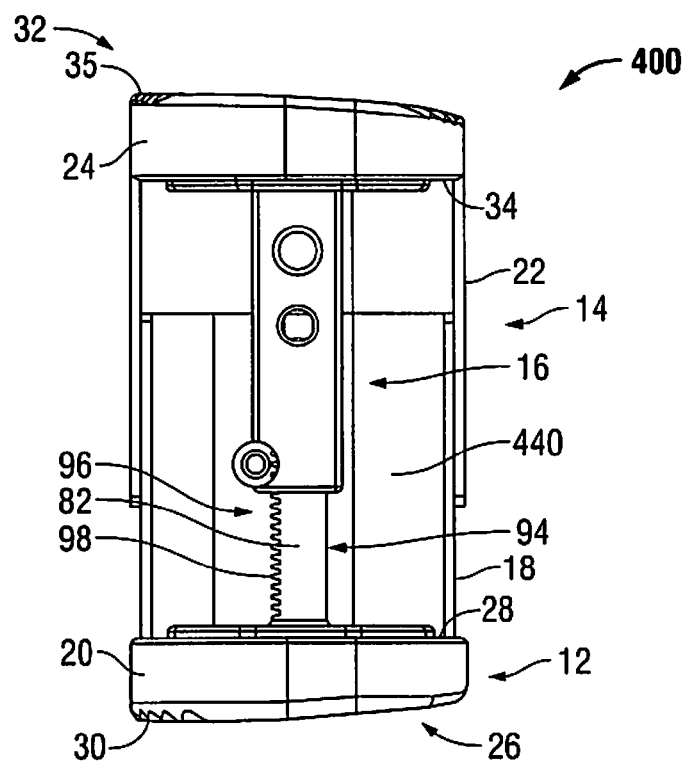
FIG. 20 is a front view of the expandable cage of FIG. 19.
Figure 21:
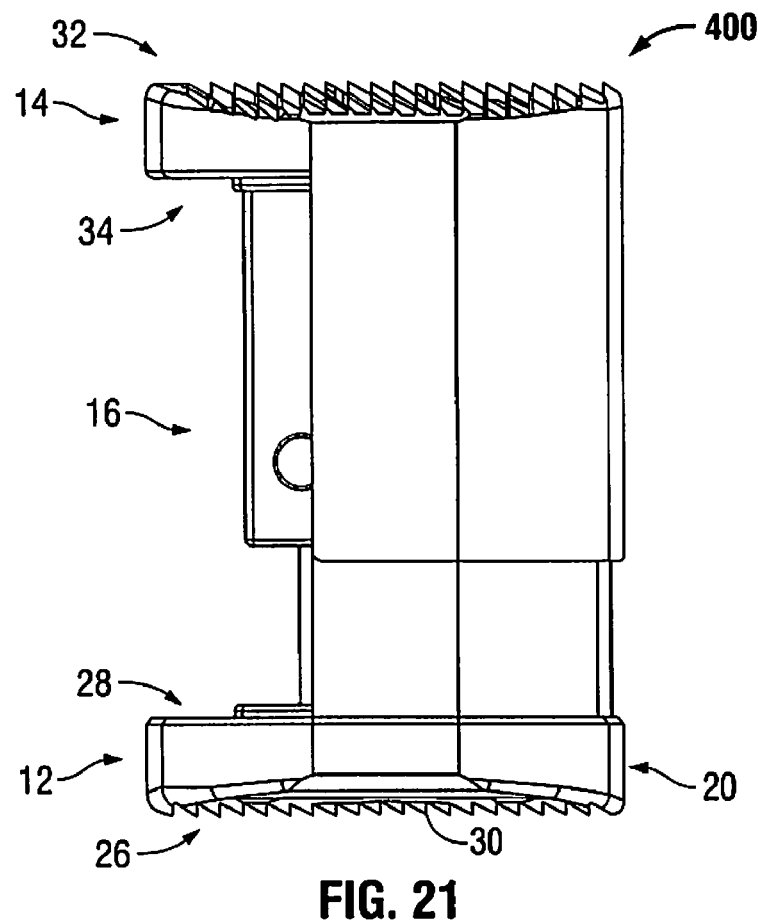
FIG. 21 is a side view of the expandable cage of FIG. 19.
Figure 22:
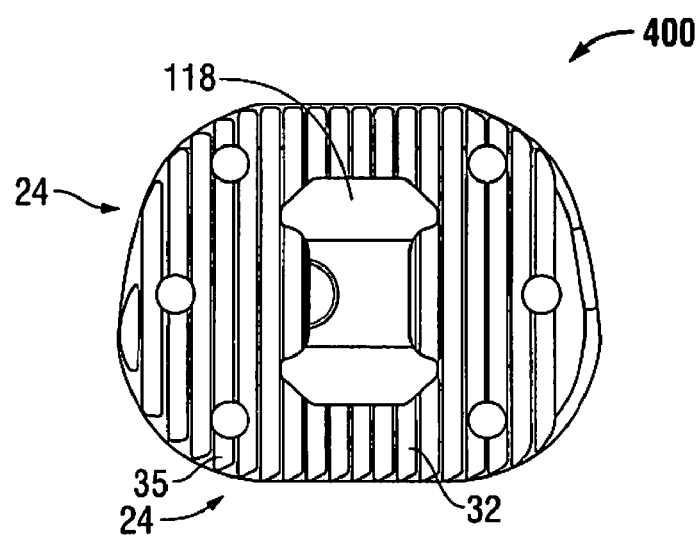
FIG. 22 is a top view of the expandable cage of FIG. 20.

As seen in FIG. 18, proximal wall 214 includes a first threaded hole 218 for receiving threaded section 210t of a distal portion 210d of rod 210 and a second threaded hole 220 for receiving a driving bolt 222. When holding portion 208 is attached to connecting member 16, first threaded hole 218 is longitudinally aligned with threaded hole 108 and second threaded hole 220 is longitudinally aligned with longitudinal opening 110 of connecting member 16. In operation, first threaded hole 218 mates with threaded section 210t of rod 210 in response to a rotation of second handle 204. Similarly, second threaded hole 220 mates with driving bolt 222 upon rotation of driving bolt 222.

Holding portion 208 further contains a tubular member 224 for retaining driving bolt 222. A pin 229, or any other suitable fastening device, interconnects tubular member 224 and elongate body 206. Tubular member 224 extends proximally from proximal wall 214 and includes a bore 226 substantially aligned with second threaded hole 220 (See FIG. 18). Bore 226 is dimensioned to receive driving bolt 222.

Figure 15:
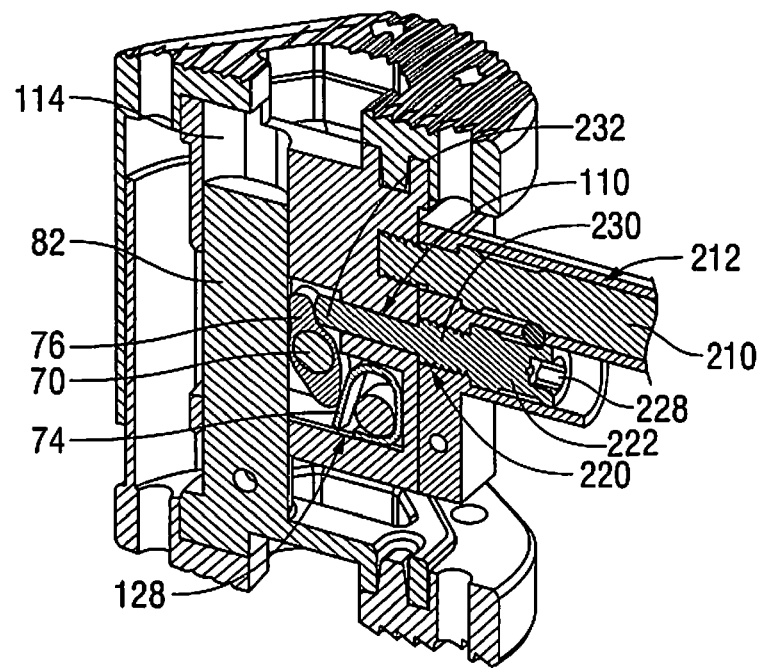
FIG. 15 is perspective cross-sectional view of a portion of the tool of FIG. 11 attached to expandable cage of FIG. 1, showing a cam lock in the unlocked position.

Driving bolt 222 includes a socket 228 disposed on a proximal portion thereof, a central threaded section 230, and a blunt distal tip 232 without threads. Socket 228 is adapted to receive a driver 300. (See FIG. 13). Central threaded section 230 is located between socket 228 and blunt distal tip 232 and, in operation, mates with second threaded hole 220 when driving bolt 222 rotates. In use, blunt distal tip 232 pushes a portion of camming member 76 distally, causing camming member 76 to pivot about pivot pin 70, upon rotation of driving bolt 222 with driver 300, as discussed in detail below (FIG. 15). In one embodiment, all the components of expandable cage 10 are made of PEEK except for camming member 76, column 82, and biasing member 74. It is also contemplated that first and second supporting members 12, 14 are formed from PEEK, while the connecting member 16 is formed from a suitable biocompatible material such as titanium or stainless steel.

Figure 13:
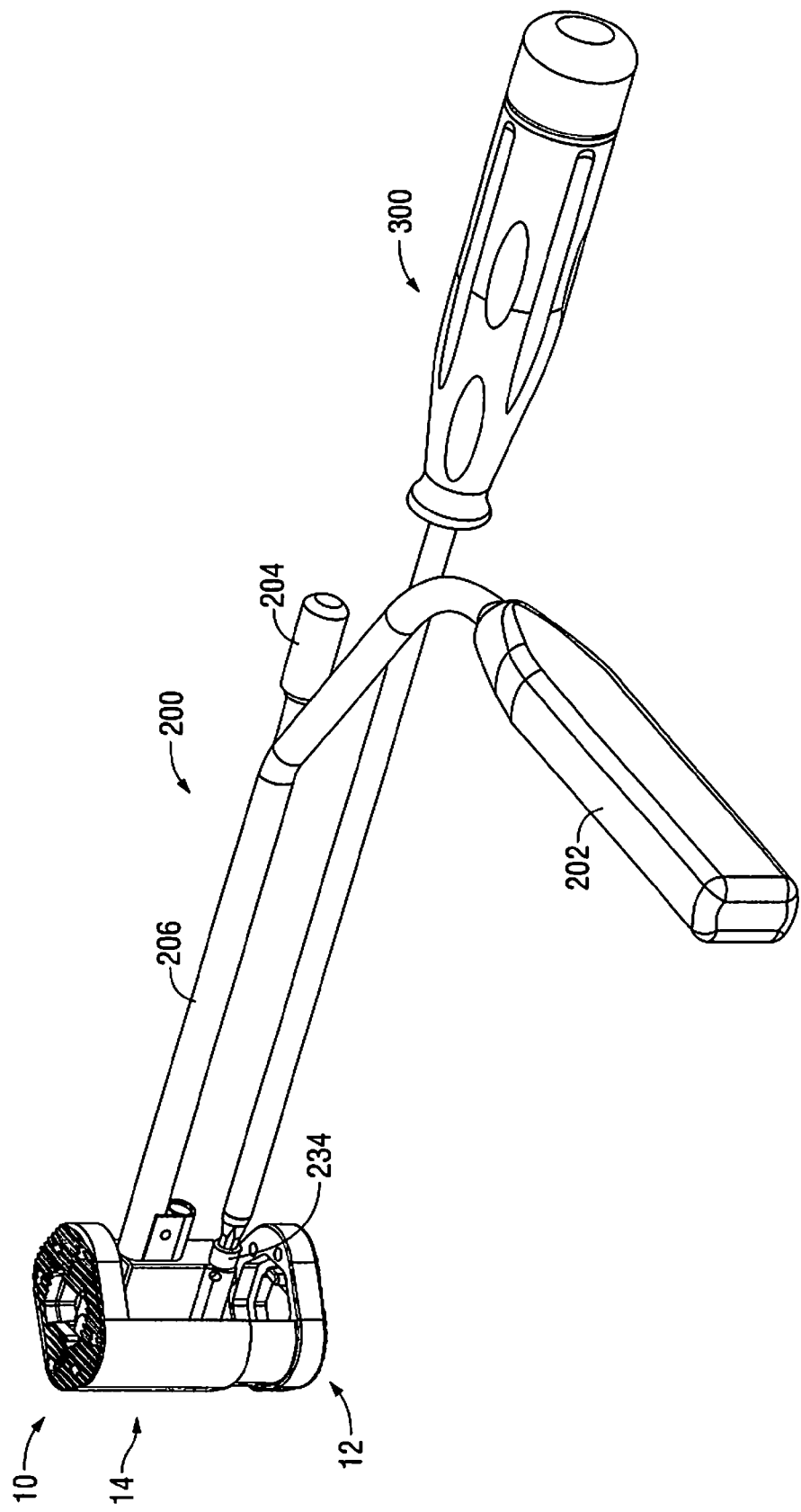
FIG. 13 is a perspective view of the tool of FIG. 11 expanding the expandable cage of FIG. 1.
Figure 14:
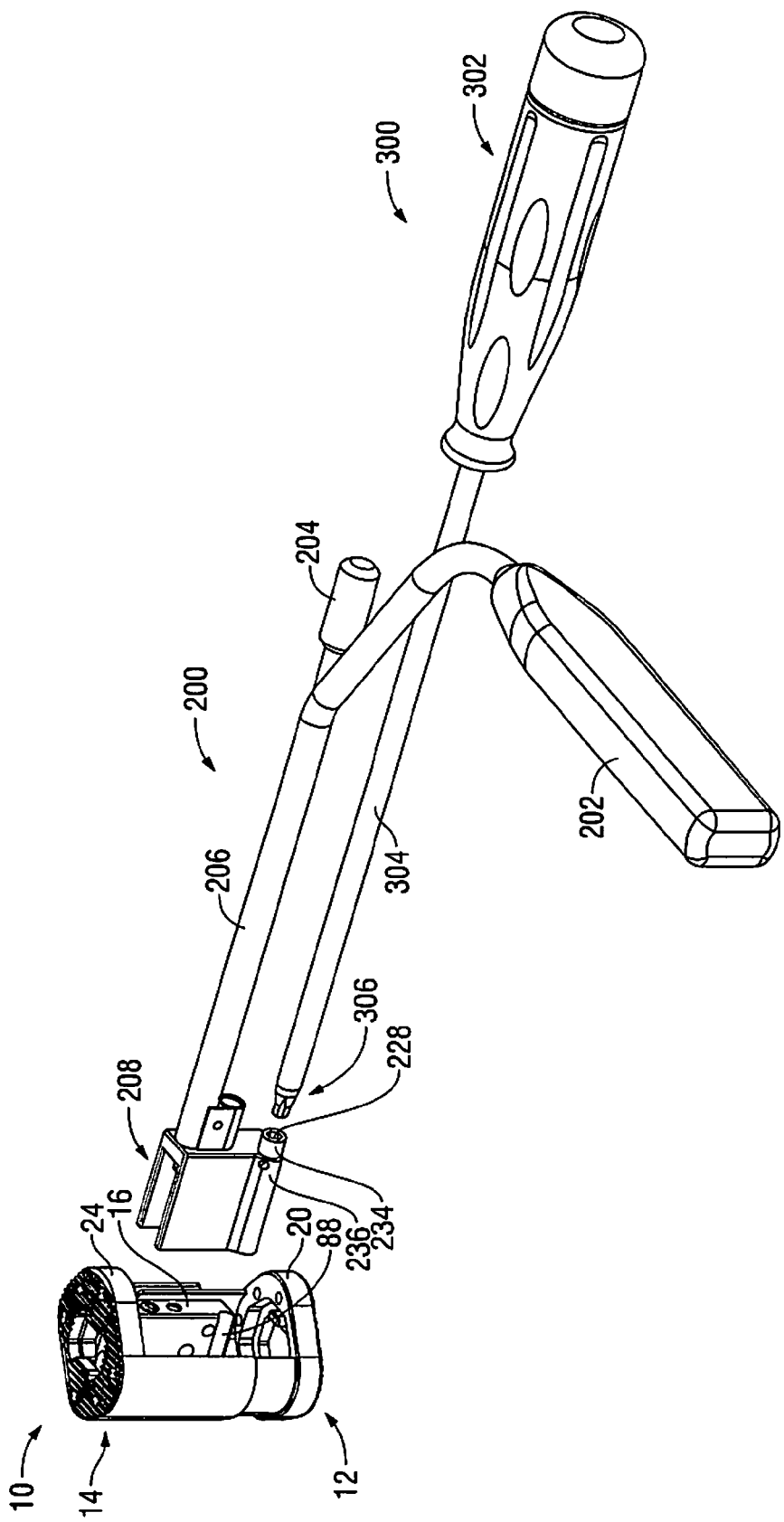
FIG. 14 is a perspective view of the tool of FIG. 11 detached from the expandable cage of FIG. 1 after expansion.

Referring to FIGS. 13 and 14, users may also employ driver 300 to rotate an elongate pinion 234 disposed in a cylindrical member 236 of holding portion 208. Cylindrical member 236, which is located on a lower section of holding portion 208, defines a bore (not shown) for receiving elongate pinion 234 and is adapted to be at least partially received in arc-shaped recess 88 of connecting member 16. When arms 216 of holding portion 208 are placed around connecting member 16, cylindrical member 236 lies on arc-shaped recess 88. Cylindrical member 236 additionally includes an opening (not shown) uncovering at least a portion of elongate ring 234. This opening is at least partially aligned with opening 92 leading to rack 98. Such alignment allows rack 98 to mesh with elongate pinion 234. Rotating elongate pinion 234 causes rack 98 to move linearly. Elongate pinion 234 includes a socket 238 positioned in a proximal portion thereof. Socket 238 is configured to receive a portion of driver 300.

Driver 300 may be a regular screwdriver. In the embodiment depicted in FIGS. 13 and 14, driver 300 includes a handle 302, a head 306, and a rod 304 coupling handle 302 to head 306. Head 306 is configured to be received within socket 238 of elongate pinion 234 or socket 228 of driving bolt 222. During operation, the user can employ driver 300 to rotate driving bolt 222 and elongate pinion 234. As discussed below, the rotation of elongate pinion 234 causes the longitudinal movement of first and second supporting members 12, 14 with respect to each other, while the rotation of driving bolt 222 engages and disengages cam lock mechanism 128 to lock or unlock the relative position of first and second supporting members 12, 14.

With references to FIGS. 11-18, since first and second supporting members 12, 14 are moveable relative to each other, expandable cage 10 can adjust its height infinitely over a pre-defined range and is therefore suitable for use in intervertebral spaces of different sizes. In spine surgery, a surgeon may use tool 200, or any other appropriate apparatus, to insert and expand expandable cage 10. Before expanding expandable cage 10, the surgeon advances holding porting 208 of tool 200 toward connecting member 16 of expandable cage 10 to hold expandable cage 10 with tool 200, as shown in FIG. 11. Arms 216 of holding portion 208 surround connecting member 16 and cylindrical member 234 rests on arc-shaped recess 88 when tool 200 grasps connecting member 16 of expandable cage 10, as seen in FIG. 12. Subsequently, the surgeon rotates rod 210 clockwise via second handle 204 to threadedly secure distal portion 210d of rod 210 inside first threaded hole 218. As rod 210 rotates clockwise, the threaded section 210t of distal portion 210d mates with first threaded hole 218, thereby securing holding portion 208 to connecting member 16. After properly attaching holding portion 208 to connection member 16, the surgeon can expand expandable cage 10 once expandable cage 10 has been positioned between adjacent vertebrae. Prior to the insertion of expandable cage 10, the surgeon removes tissue between adjacent vertebrae to form an intervertebral space. The dimensions of this intervertebral space may vary. The surgeon may nonetheless change the height of expandable cage 10 with tool 200 and driver 300 to accommodate expandable cage 10 within this intervertebral space after inserting expandable cage 10 in the intervertebral space formed between adjacent vertebrae.

Following the insertion of expandable cage 10 in the intervertebral space, the surgeon changes the relative position of first and second supporting members 12, 14 to expand expandable cage 10. If the cam lock mechanism 128 is disengaged, as depicted in FIG. 15, the surgeon can move first and second supporting members 12, 14 relative to each other to adjust the height of expandable cage 10. When cam lock mechanism 128 is disengaged, camming member 76 is in a first position, as shown in FIG. 15, and does not engage column 82 in such a way that precludes movement of column 82 along longitudinal opening 114. To the contrary, camming member 76 allows column 82 to move freely within longitudinal opening 114 when cam lock mechanism 128 is disengaged. The surgeon disengages cam lock mechanism 128 by rotating driving bolt 222 with driver 300. Specifically, the surgeon first inserts head 306 of driver 300 in socket 228 and then rotates driving bolt 222 clockwise to translate threaded faster 222 distally along longitudinal opening 110. As driving bolt 222 rotates clockwise, its central threaded section 230 mates with second threaded hole 220 to secure threaded fastener in a distal position, as illustrated in FIG. 15. While driving bolt 222 moves toward the distal position, blunt tip 232 pushes distally a portion of camming member 76, causing camming member 76 to pivot to the first position against the bias of biasing member 74 (See FIG. 15). When the camming member 76 is in the first position, cam lock mechanism 128 is disengaged from column 88 and permits first and second supporting members 12, 14 to translate relative to one another.

As seen in FIG. 13, the surgeon introduces head 306 of driver 300 into socket 238 of elongate pinion 234 and then rotates elongate pinion 234 with driver 300 to adjust the relative position of first and second supporting members 12, 14. Rotating driver 300 causes elongate pinion 234 to rotate. Elongate pinion 234 engages with rack 98 (see FIG. 1) upon a rotation of driver 300. In particular, a clockwise rotation of elongate pinion 234 causes the displacement of connecting member 16 away from first support plate 20. While connecting member 16 moves away from first support plate 20, first and second walls 18, 22 translate with respect to each other, thereby increasing the distance between first support plate 20 and second support plate 24 (See FIG. 16). The surgeon adjusts the distance between first and second support plates 20, 24 (and, consequently, the relative position of first and second support members 12, 14) until teeth 30, 36 of first and second support plates 20, 24 engage vertebral tissue.

Once first and second support plates 20, 24 frictionally engage vertebral tissue, the surgeon places cam lock mechanism 128 in the locked position to hinder the relative motion of first and second supporting members 12, 14. To move cam lock mechanism 128 to the locked position, the surgeon rotates driving bolt 222 counterclockwise with driver 300. Rotating driving bolt 222 counterclockwise causes the proximal translation of driving bolt 222. As driving bolt 222 moves proximally, biasing member 74 biases a portion of camming member 76 toward column 82, as seen in FIG. 16. Eventually, said portion of camming member 76 frictionally engages column 82 under the influence of biasing member 74 and substantially hinders the movement of column 82 along longitudinal opening 114. At this moment, cam lock mechanism 128 maintains first and second supporting members 12, 14 in a fixed relative position. The surgeon can unlock cam lock mechanism 128 (see FIG. 15), readjust the relative position of first and second support members 12, 14, and re-lock cam lock mechanism 128 as many times as desired (See FIG. 17).

Immediately after securing first and second supporting members 12, 14 in the desired relative position, the surgeon detaches tool 200 from expandable cage 10. Rotating rod 210 counterclockwise via second handle 204 disengages threaded section 210t of distal portion 210d from threaded hole 108 and moves rod 210 proximally. As soon as rod 210 has been removed from threaded hole 108, the surgeon can disconnect tool 200 from expandable cage 10, as seen in FIG. 18. Optionally, the surgeon packs expandable cage 10 and/or the intervertebral space with bone support matrix for promoting spinal fusion between adjacent vertebrae. Expandable cage 10 can be used in an anterior, posterior-lateral or lateral approach spine surgery.

FIGS. 19-22 show an expandable cage 400 for use in lateral approach spine surgery. Since the structure and operation of expandable cage 400 is substantially similar to the structure and operation of expandable cage 10, the present disclosure does not discuss in detail the particulars of expandable cage 400. In contrast to expandable cage 10, first and second supporting members 12, 14 of expandable cage 400 are positioned so that the first and second walls 18, 22 define an opening 440 leading to connecting member 16 that is aligned with one of the narrower sides 24n of second supporting plate 24.

Figure 23:
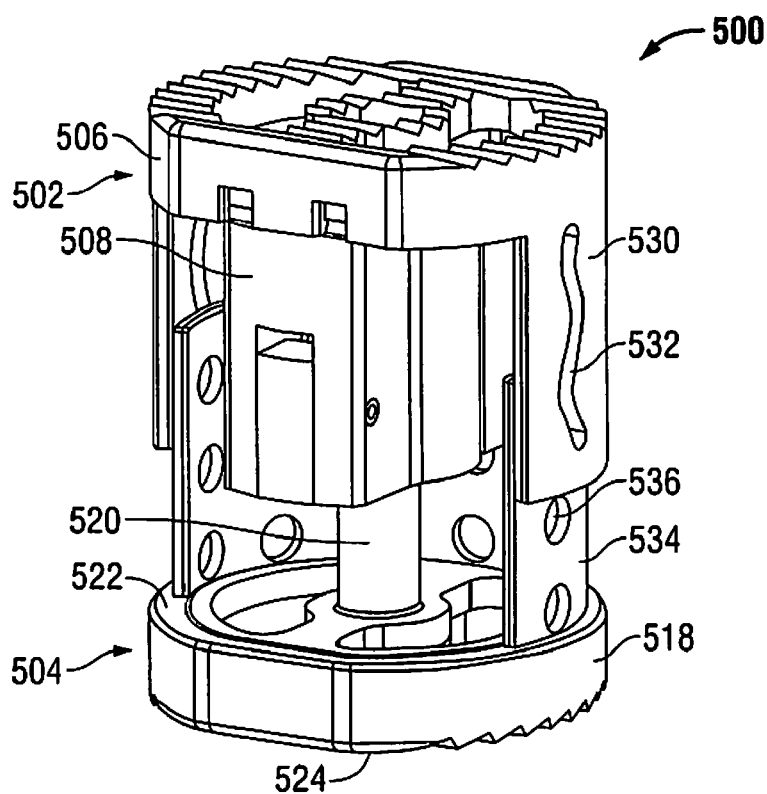
FIG. 23 is a perspective view of an expandable cage according to another embodiment of the present disclosure.
Figure 24:
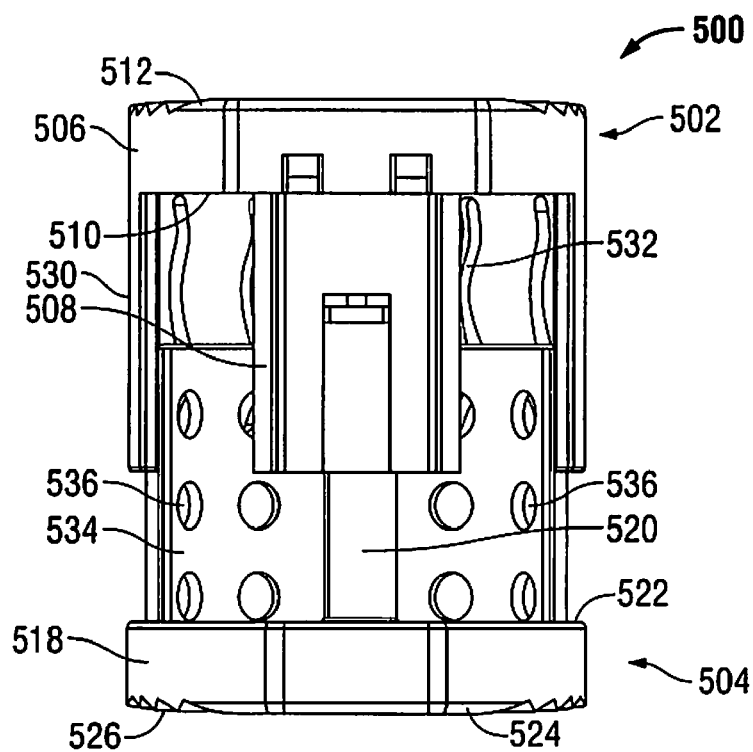
FIG. 24 is a front view of the expandable cage of FIG. 23.
Figure 25:
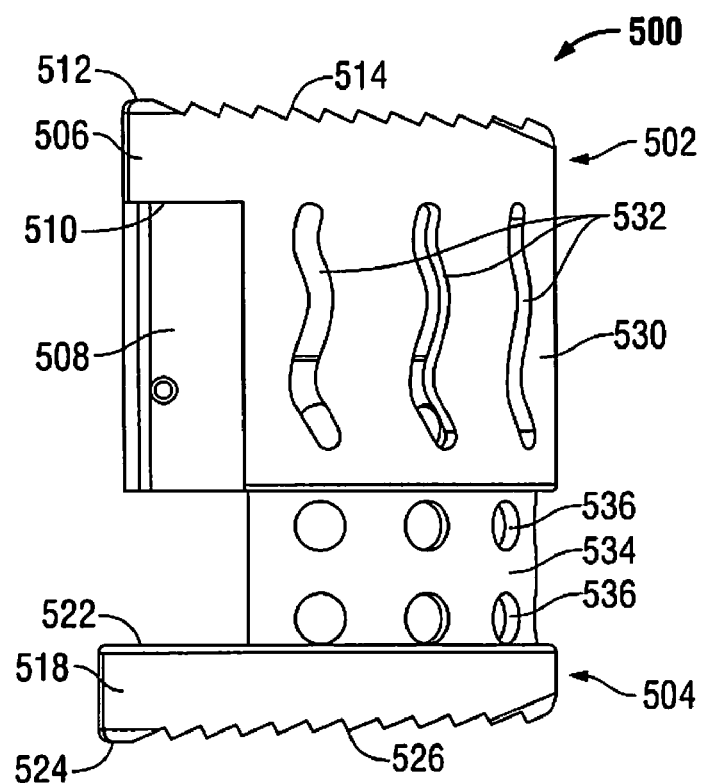
FIG. 25 is a side view of the expandable cage of FIG. 23.

With reference to FIGS. 23-25, another embodiment of an expandable cage is designated with reference numeral 500. Expandable cage 500 includes a first supporting member 502 and a second supporting member 504. First and second supporting members 502, 504 are adapted to move relative to each other between a first or collapsed position and a second or expanded position. In particular, first supporting member 502 includes a first end plate 506 and an elongate body 508 extending toward second supporting member 504. Elongate body 508 extends from the first end plate 506. First end plate 506 includes an inner surface 510 facing elongate body 508 and an outer surface 512 facing away from elongate body 508. Inner surface 510 of first end plate 506 is connected to elongate body 508. Outer surface 512 incorporates a plurality of teeth 514 protruding therefrom. Teeth 514 are slanted at an oblique angle relative to inner surface 510.

Figure 26:
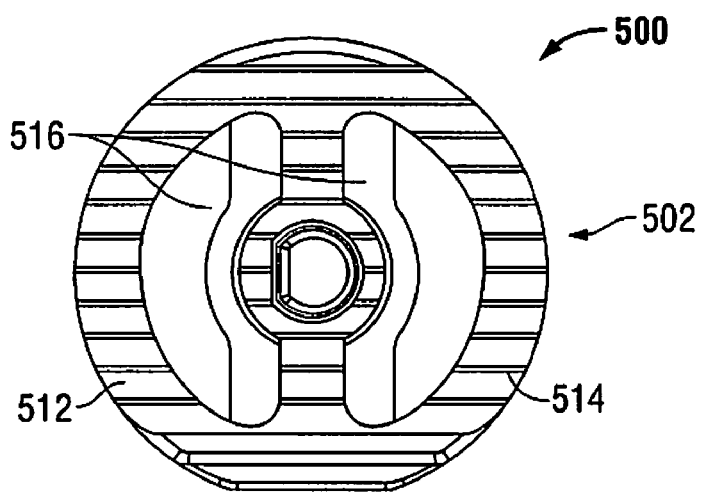
FIG. 26 is a top view of the expandable cage of FIG. 23.

As seen in FIG. 26, first end plate 506 further includes a pair of apertures 516 extending therethrough. Apertures 516 promote bone growth when expandable cage 500 is placed between vertebral bodies. Although the figures depict apertures 516 having hemispherical shape, apertures 516 may have any suitable shape or configuration.

With continued reference to FIGS. 23-25, second supporting member 504 includes a second end plate 518 and a column 520 extending toward first supporting member 502. Second end plate 518 includes an inner surface 522 facing column 520 and an outer surface 524 facing away from column 520. Outer surface 524 has a plurality of teeth 526 protruding therefrom. Teeth 526 are slanted at an oblique angle relative to inner surface 522.

Figure 30:
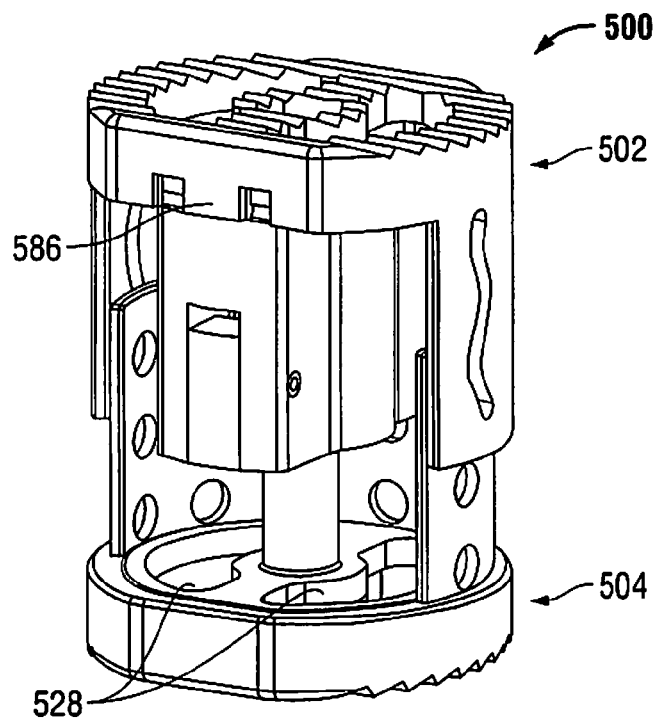
FIG. 30 is a perspective view of the expandable cage of FIG. 23 in the expanded position.
Figure 31:
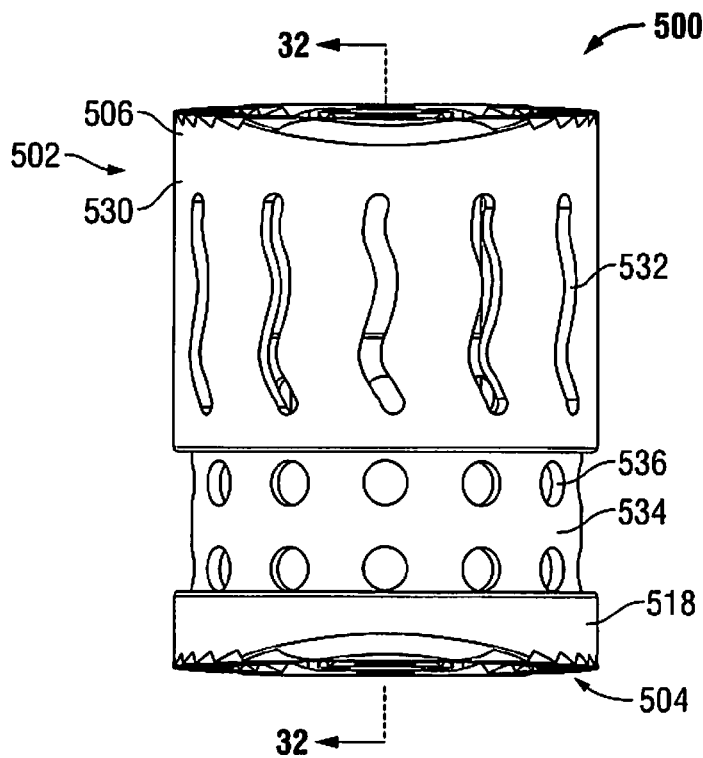
FIG. 31 is a rear view of the expandable cage of FIG. 23.

As seen in FIG. 30, second end plate 504 includes a pair of apertures 528 extending therethrough. Apertures 528 promote bone growth when expandable cage 500 is positioned between vertebral bodies. While the figures show apertures 528 having a hemispherical shape, apertures 528 may have any suitable shape or configuration.

Returning to FIGS. 23-25, first supporting member 502 includes a first wall 530 extending from inner surface 510 of first end plate 506. First wall 530 partially surrounds elongate body 508 and extends toward second supporting member 504. In one embodiment, first wall 530 includes a plurality of slots 532 having a sinusoidal shape. Slots 532 span across first wall 530 and promote bone growth when expandable cage 500 is placed between vertebral bodies. In use, first wall 530 facilitates relative motion of first and second supporting members 502, 504.

Second supporting member 504 includes a second wall 534 extending from inner surface 522 of second end plate 518. Second wall 534 partially surrounds column 520 and extends toward first supporting member 502. In an embodiment, second wall 534 has a plurality of circular holes 536 for promoting bone growth. Circular holes 536 span across second wall 534.

As seen in FIGS. 23 and 24, first wall 530 is adapted to slidably receive second wall 534. When a user expands or collapses expandable cage 500, first and second walls 530, 534 slide relative to each other and guide the relative movement of first and second supporting members 502, 504.

Figure 27:
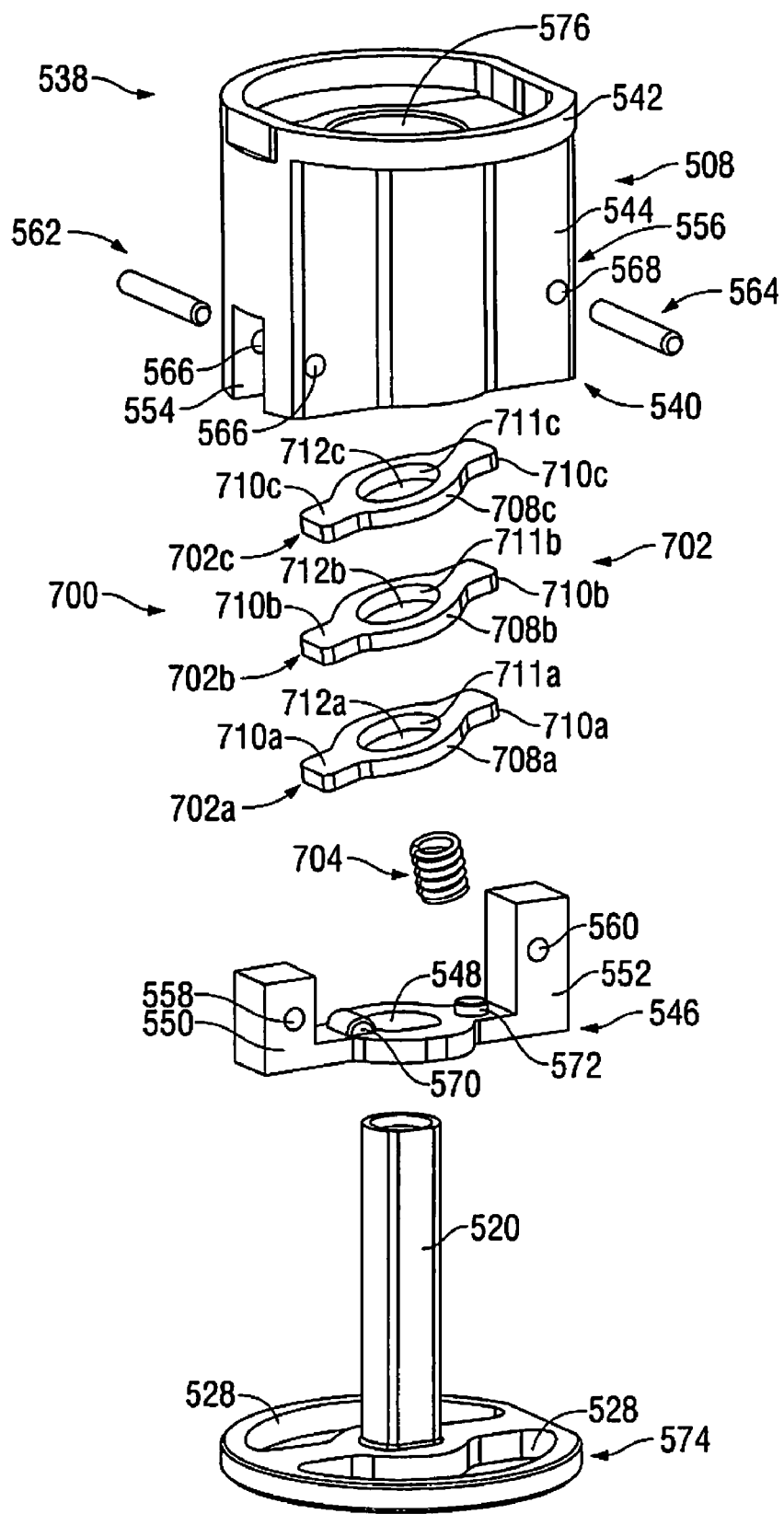
FIG. 27 is a perspective exploded view of an inner portion of the expandable cage of FIG. 23.
Figure 28:
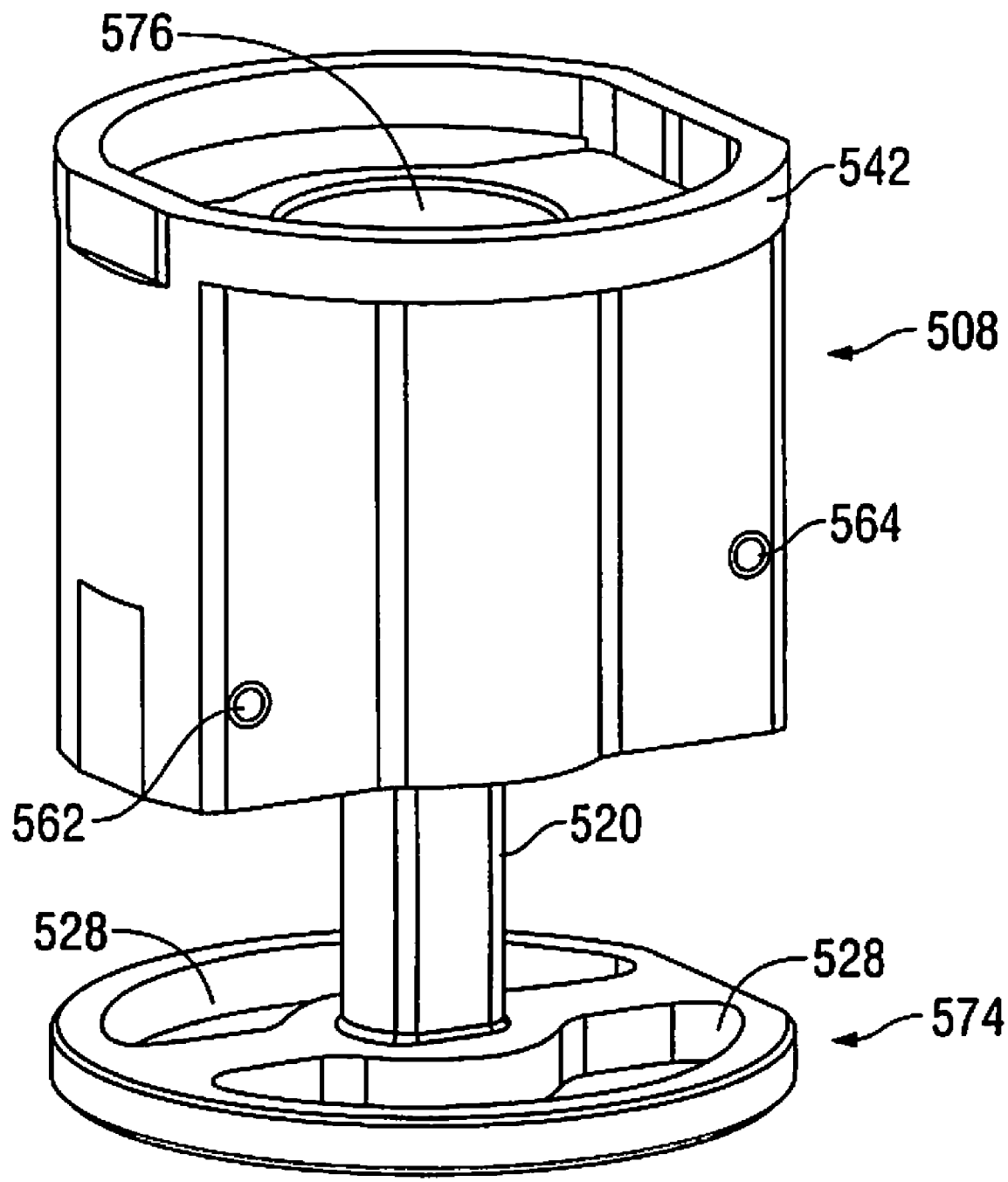
FIG. 28 is a perspective view of the inner portion of the expandable cage of FIG. 23.
Figure 29:
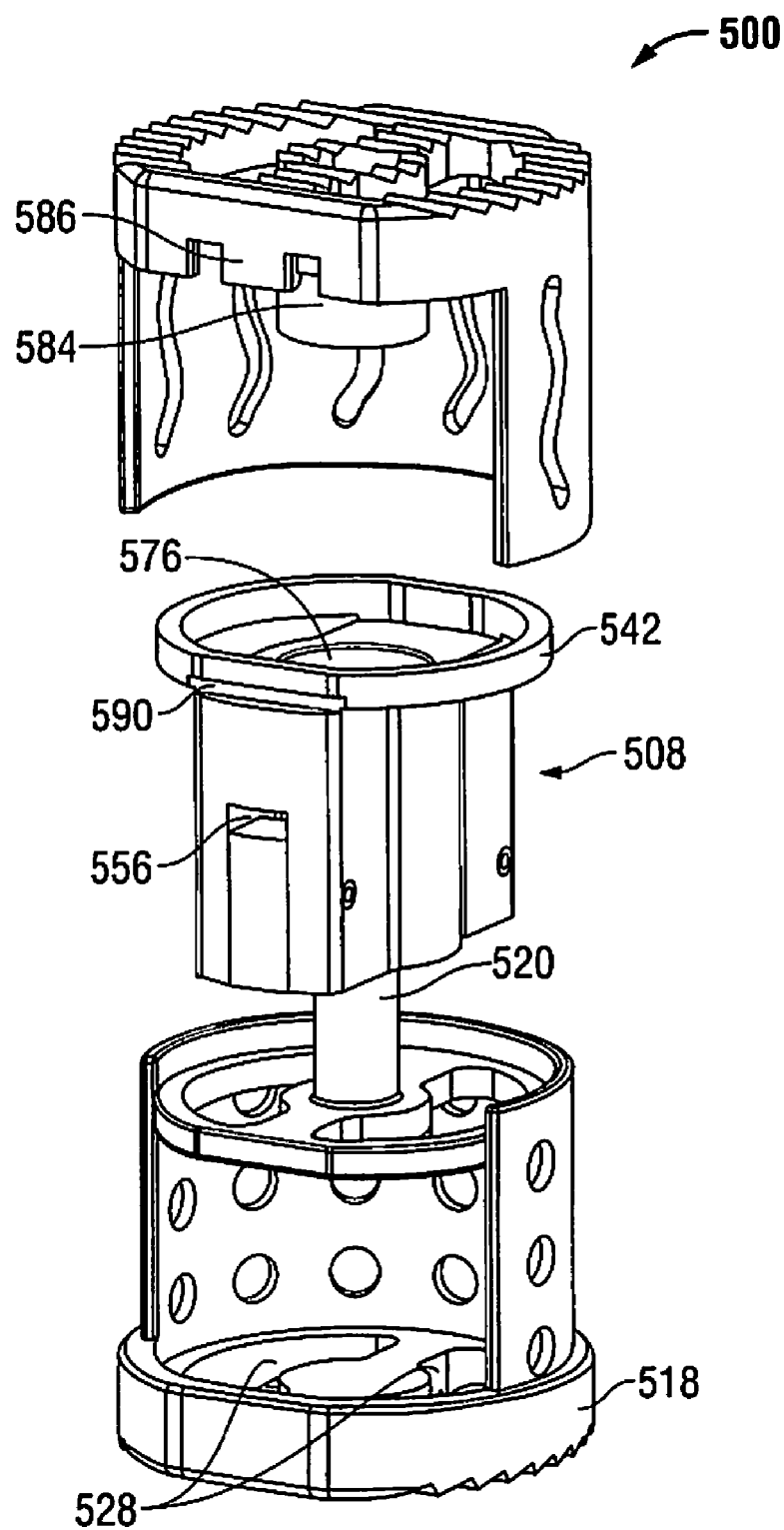
FIG. 29 is a perspective exploded view of the expandable cage of FIG. 23.

With reference to FIGS. 27 and 28, elongate body 508 of first supporting member 502 has a first end 538 adapted to be operatively connected to first end plate 506 and a second end 540 spaced apart from first end plate 506. (See FIG. 29). Elongate body 508 includes a connecting section 542 located at the first end 538. Connecting section 542 has substantially circular shape and is configured to be coupled to first end plate 506. Elongate body 508 further includes a middle section 544 positioned between first and second ends 538, 540 and a base 546 located on second end 540.

Base 546 of elongate body 508 includes an opening 548 dimensioned to receive column 520 and first and second lugs 550, 552 adapted to be positioned in first and second slots 554, 556 of elongate body 508. First and second lugs 550, 552 are located on opposite sides of base 546. First lug 550 has a first hole 558 adapted to receive a first pin 562, and second lug 552 has a second hole 560 adapted to receive a second pin 564. First lug 550 is shorter than second lug 552.

Elongate body 508 has a pair of first openings 566 located adjacent to first slot 554 and a pair of second openings 568 positioned adjacent to second slots 556. First openings 566 are dimensioned to receive first pin 562, and second openings 568 are dimensioned to receive second pin 564. When first lug 550 is positioned inside first slot 554 of elongate body 508, first openings 566 are aligned with first hole 558 of first lug 550. When second lug 552 is positioned inside second slot 556 of elongate body 508, second openings 568 are aligned with second hole 560 of second lug 552. First pin 562 is inserted through first openings 566 and first hole 558 and second pin 564 is inserted through second openings 568 and second hole 560 to assemble elongate body 508, as shown in FIG. 28.

Base 546 further includes a protuberance 570 adjacent to first lug 550 and a protrusion 572 adjacent to second lug 552. In the embodiment depicted in FIG. 27, protuberance 570 has a semi-circular cross-section and projection 572 has a cylindrical shape. Protuberance 570 and projection 572 may nevertheless have any suitable shape or configuration. Protuberance 570 is adapted to abut a ring plate 702 of a ring plate lock mechanism 700. Projection 752 is adapted to retain a biasing member 704, such as a spring, of ring plate lock mechanism 700.

As seen in FIG. 27, ring plate lock mechanism 700 is positioned inside elongate body 508. In operation, ring plate lock mechanism 700 maintains first and second supporting members at a fixed relative position. Ring plate lock mechanism 700 includes a plurality of ring plates 702 and biasing member 704 operatively associated with ring plates 702. In the embodiment illustrated in FIG. 27, ring plate lock mechanism 700 includes three ring plates 702, namely first ring plate 702a, second ring plate 702b, and third ring plate 702c. Ring plate lock mechanism 700 may nonetheless have more or fewer ring plates 702.

Ring plates 702a, 702b, and 702c are substantially similar to one another. Ring plate 702a, however, includes a projection 706 (see FIG. 32) extending toward biasing member 704. Projection 706 is adapted to retain biasing member 704. Projections 572 of base 546 and projection 706 of ring plate lock mechanism 700 collectively secure biasing member 704 within elongate body 508.

Aside from projection 706, ring plates 702a, 702b, and 702c are substantially similar to one another. Each of the ring plates 702a, 702b, 702c includes a pair of a circular body 708a, 708b, 708c and a pair of planar extensions 710a, 710b, 710c protruding from opposite sides of circular body 708a, 708b, 708c. Each circular body 708a, 708b, 708c includes an inner surface 711a, 711b, 711c. Each inner surface 711a, 711b, 711c forms an opening 712a, 712b, 712c dimensioned to receive column 520.

Ring plates 702 are collectively configured to move between a first or unlocked position and a second or locked position. In the first position, ring plates 702 are oriented substantially perpendicular with respect to column 520. When ring plates 702 are oriented in the first or unlocked position, elongate body 508 can move freely along column 520 and therefore allows first and second supporting members 502, 504 to move relative to each other. In the second or locked position, ring plates 702 are oriented at an oblique angle relative to column 520. In the second or locked position, inner surfaces 711a, 711b, 711c frictionally engage column 520, thereby inhibiting or preventing column 520 from moving with respect to rings plates 702. Therefore, when ring plates 702 are oriented in the second position, elongate body 508 is hindered or prevented from moving along column 520 and thus first and second supporting members 502, 504 are maintained at a fixed relative position. (See FIG. 32).

Figure 32:
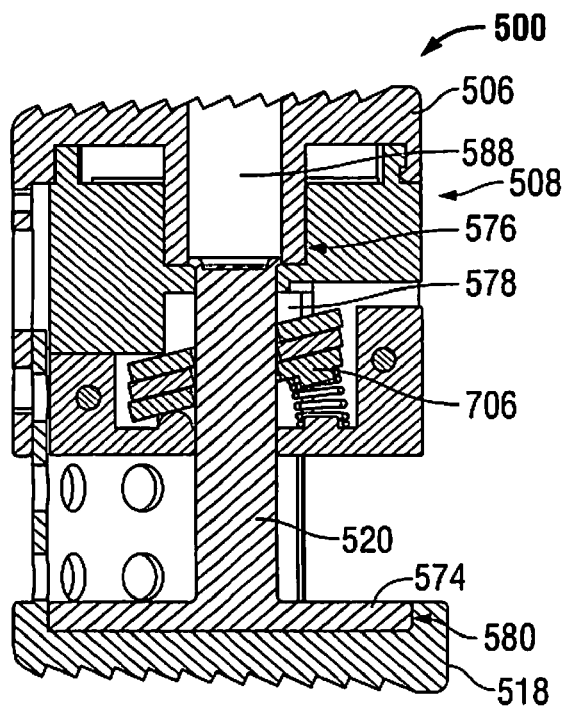
FIG. 32 is a cross-sectional view of the expandable cage of FIG. 23, taken along line 32-32 of FIG. 31.

As seen in FIG. 28, elongate body 508 further includes a longitudinal opening 576 adapted to receive column 520. Longitudinal opening 576 leads to an inner cavity 578 (FIG. 32) dimensioned to accommodate ring plate lock mechanism 700 and column 520. Column 520 is connected to a column support 576. As seen in FIG. 32, column support 576 is configured to be coupled to second end plate 518 and includes a pair of openings 580. Second end plate 518 has a recess adapted to securely receive column support 574. When column support 574 is placed on recess 582 of second end plate 518, openings 580 are aligned with apertures 528 of second end plate 518, as depicted in FIG. 30.

With reference to FIGS. 29-32, first supporting member 502 includes connecting section 584 protruding from first end plate 506 and a snap-fit detent 586 for facilitating connection between first supporting member 502 and elongate body 508. As seen in FIG. 32, connecting section 584 has a bore 588 extending therethrough and is configured to be positioned inside longitudinal opening 576 of elongate body 508. Bore 588 is dimensioned to receive column 520. Snap-fit detent 586 is adapted to be received in notch 590 of elongate body 508 to secure first supporting member 502 to elongate body 508.

In one embodiment, first supporting member 502, second supporting member 504, and ring plates 702 are made of titanium alloy or any other suitable biocompatible metal capable of withstanding the normal forces of the spine. In another embodiment, first supporting member 502, second supporting member 504, and ring plates 702 are made of polyetheretherketone (PEEK) or any other suitable biocompatible plastic or material.

Figure 33:
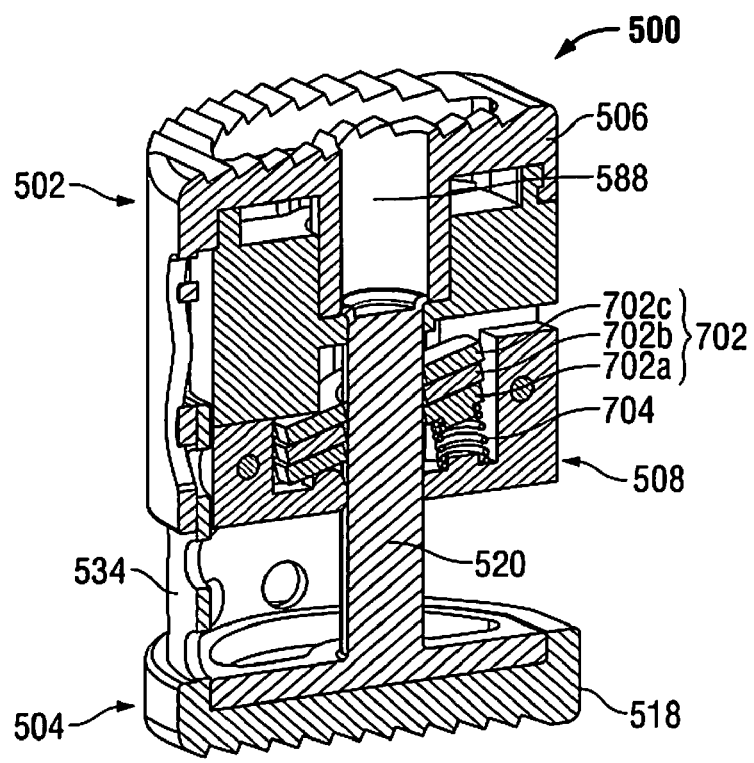
FIG. 33 is a perspective cross-sectional view of the expandable cage of FIG. 23.

With reference to FIG. 33, a user can use expandable cage 500 for spinal or orthopedic surgical procedures. In one exemplary application, first and second supporting members 502, 504 of expandable cage 500 are initially oriented in the first or collapsed position. When first and second supporting members 502, 504 are in the first position, ring plates 702 are in oriented substantially perpendicular to column 520, thereby allowing column 520 to move freely through openings 712a, 712b, 712c of ring plates 702a, 702b, 702c. The user accesses a patient's spine and removes diseased vertebral tissue located between adjacent vertebrae to create a void. Subsequently, the user places expandable cage 500 in the void formed between adjacent vertebrae and packs the remaining space of the void and/or expandable cage 500 with bone support matrix. After expandable cage 500 has been properly positioned between adjacent vertebrae, the user employs any suitable means or device, such as a distracting instrument, to move first and second supporting members 502, 504 away from each other (i.e., toward the second or expanded position) until first and second end plates 506, 518 engage the adjacent vertebral bodies. While first and second supporting members 502, 504 move toward the second position, ring plates 702 tilt toward their second or locked position, defining an oblique angle relative to column 520. In the second or locked position, inner surfaces 711a, 711b, 711c of ring plates 702a, 702b, 702c frictionally engage column 520, thereby inhibiting or preventing column 520 from moving with respect to rings plates 702. As additional compressive forces are exerted on first and second support members 502, 504, ring plates 702 exert an opposite force that further inhibits first and second supporting members 502, 504 from moving to the first collapsed position.

It will be understood that various modifications may be made to the embodiments of the presently disclosed expandable cage and tool. For instance, expandable cage 500 may include a set screw, or any other suitable mechanical stop, positioned in elongate body 508 to hinder or prevent further relative movement of first and second supporting members 502, 504 once the first and second supporting members 502, 504 have been placed in the second or expanded position. Therefore, the above description should not be construed as limiting, but merely as exemplifications of embodiments. Those skilled in the art will envision other modifications within the scope and spirit of the present disclosure.

What is claimed is:

1. An apparatus for spinal surgery, comprising:
a first supporting member configured to engage tissue;
a second supporting member configured to engage tissue and operatively associated with the first supporting member, wherein the first and second supporting members are movable relative to each other; and
a lock mechanism, the lock mechanism including:
a camming member rotatable about a pivot pin between a locked condition, wherein the camming member engages at least one of the first and second supporting members to maintain the first and second supporting members in a fixed relative position, and an unlocked condition, wherein the camming member is rotated out of engagement with the at least one of the first and second supporting members to permit movement of the first and second supporting members relative to one another;
a biasing member configured to bias the camming member towards the locked condition; and
a fastener operably positioned relative to the camming member, the fastener movable between a first position, wherein the fastener is spaced-apart from the camming member allowing the biasing member to bias the camming member towards the locked condition, and a second position, wherein the fastener is in contact with and urges the camming member against the bias of the biasing member towards the unlocked condition, the fastener threadingly engaged within a threaded opening such that rotation of the fastener in a first direction moves the fastener towards the first position and such that rotation of the fastener in a second, opposite direction moves the fastener towards the second position.

2. The apparatus of claim 1, wherein the first supporting member includes a longitudinal opening and the second supporting member includes a column adapted to be slidably received in the longitudinal opening.

3. The apparatus of claim 2, wherein the camming member frictionally engages the column when located in the locked condition to maintain the first and second supporting members in fixed position relative to one another.

4. The apparatus of claim 1, wherein the first supporting member includes an elongate body extending toward the second supporting member, the elongate body having a threaded hole adapted to receive a portion of an insertion tool.

5. The apparatus of claim 4, wherein the elongate body includes an opening leading to the lock mechanism, the opening being adapted to receive a portion of the insertion tool.

6. The apparatus of claim 4, wherein the elongate body includes an arc-shaped recess extending therealong, the arc-shaped recess being adapted to receive a portion of the insertion tool.

7. The apparatus of claim 1, wherein the first and second supporting members are movable relative to each other along an expansion axis, and wherein the camming member is rotatable about a pivot axis of the pivot pin, the pivot axis disposed in transverse relation relative to the expansion axis.

8. The apparatus of claim 1, wherein the fastener defines a socket for receiving a driving tool for moving the fastener between the first and second positions.

9. The apparatus of claim 1, wherein the camming member includes a first end, a second end, and a middle portion, the pivot pin extending through the middle portion of the camming member.

10. The apparatus of claim 9, wherein the biasing member is configured to contact the camming member towards the first end thereof to bias the camming member towards the locked condition, and wherein the fastener is configured to contact the camming member towards the second end thereof to urge the camming member against the bias of the biasing member towards the unlocked condition.

11. An apparatus for spinal surgery, comprising:
a first supporting member configured to engage tissue;
a second supporting member configured to engage tissue;
a telescoping connecting member operatively associated with the first and second supporting members, such that the first and second supporting members are movable relative to each other; and
a lock mechanism associated with the telescoping connecting member, the lock mechanism including:
a camming member rotatable about a pivot pin between a locked condition, wherein the camming member engages the telescoping connecting member to maintain the first and second supporting members in a fixed relative position, and an unlocked condition, wherein the camming member is rotated out of engagement with the telescoping connecting member to permit movement of the first and second supporting members relative to one another;
a biasing member configured to bias the camming member towards the locked condition; and
a fastener operably positioned relative to the camming member, the fastener movable between a first position, wherein the fastener is spaced-apart from the camming member allowing the biasing member to bias the camming member towards the locked condition, and a second position, wherein the fastener is in contact with and urges the camming member against the bias of the biasing member towards the unlocked condition, the fastener threadingly engaged within a threaded opening such that rotation of the fastener in a first direction moves the fastener towards the first position and such that rotation of the fastener in a second, opposite direction moves the fastener towards the second position.

12. The apparatus of claim 11, wherein the second supporting member includes a column extending toward the first supporting member.

13. The apparatus of claim 11, wherein the first and second supporting members are movable relative to each other along an expansion axis, and wherein the camming member is rotatable about a pivot axis of the pivot pin, the pivot axis disposed in transverse relation relative to the expansion axis.

14. The apparatus of claim 11, wherein the fastener defines a socket for receiving a driving tool for moving the fastener between the first and second positions.

15. The apparatus of claim 11, wherein the camming member includes a first end, a second end, and a middle portion, the pivot pin extending through the middle portion of the camming member.

16. The apparatus of claim 15, wherein the biasing member is configured to contact the camming member towards the first end thereof to bias the camming member towards the locked condition, and wherein the fastener is configured to contact the camming member towards the second end thereof to urge the camming member against the bias of the biasing member towards the unlocked condition.

* * * * *